(12) United States Patent
Brown

(10) Patent No.: US 6,186,145 B1
(45) Date of Patent: Feb. 13, 2001

(54) METHOD FOR DIAGNOSIS AND TREATMENT OF PSYCHOLOGICAL AND EMOTIONAL CONDITIONS USING A MICROPROCESSOR-BASED VIRTUAL REALITY SIMULATOR

(75) Inventor: Stephen J. Brown, Woodside, CA (US)

(73) Assignee: Health Hero Network, Inc., Mountain View, CA (US)

(*) Notice: Under 35 U.S.C. 154(b), the term of this patent shall be extended for 0 days.

(21) Appl. No.: 09/336,570

(22) Filed: Jun. 21, 1999

Related U.S. Application Data

(63) Continuation-in-part of application No. 08/958,786, filed on Oct. 29, 1997, now Pat. No. 5,913,310, which is a continuation-in-part of application No. 08/857,187, filed on May 15, 1997, now Pat. No. 5,918,603, which is a continuation of application No. 08/247,716, filed on May 23, 1994, now Pat. No. 5,678,571.

(51) Int. Cl.[7] .................................................. A61B 19/00
(52) U.S. Cl. ......................... 128/897; 128/905; 600/300
(58) Field of Search ............................. 128/897–98, 905; 600/481, 300

(56) References Cited

U.S. PATENT DOCUMENTS

| | | | | |
|---|---|---|---|---|
| 5,307,263 | * | 4/1994 | Brown | 128/898 |
| 5,678,571 | * | 10/1997 | Brown | 128/898 |
| 5,918,603 | * | 7/1999 | Brown | 128/897 |

* cited by examiner

Primary Examiner—John P. Lacyk
(74) Attorney, Agent, or Firm—Black Lowe & Graham PLLC

(57) ABSTRACT

Methods and systems for monitoring, diagnosing and/or treating psychological conditions and/or disorders in patients with the aid of computer-based virtual reality simulations. Pursuant to one preferred embodiment, a computer program product is used to control a computer. The program product includes a computer-readable medium, and a controlling mechanism that directs the computer to generate an output signal for controlling a video display device. The video display device is equipped to display representations of three-dimensional images, and the output signal represents a virtual reality simulation directed to diagnosis and/or treatment of a psychological condition and/or disorder.

28 Claims, 17 Drawing Sheets

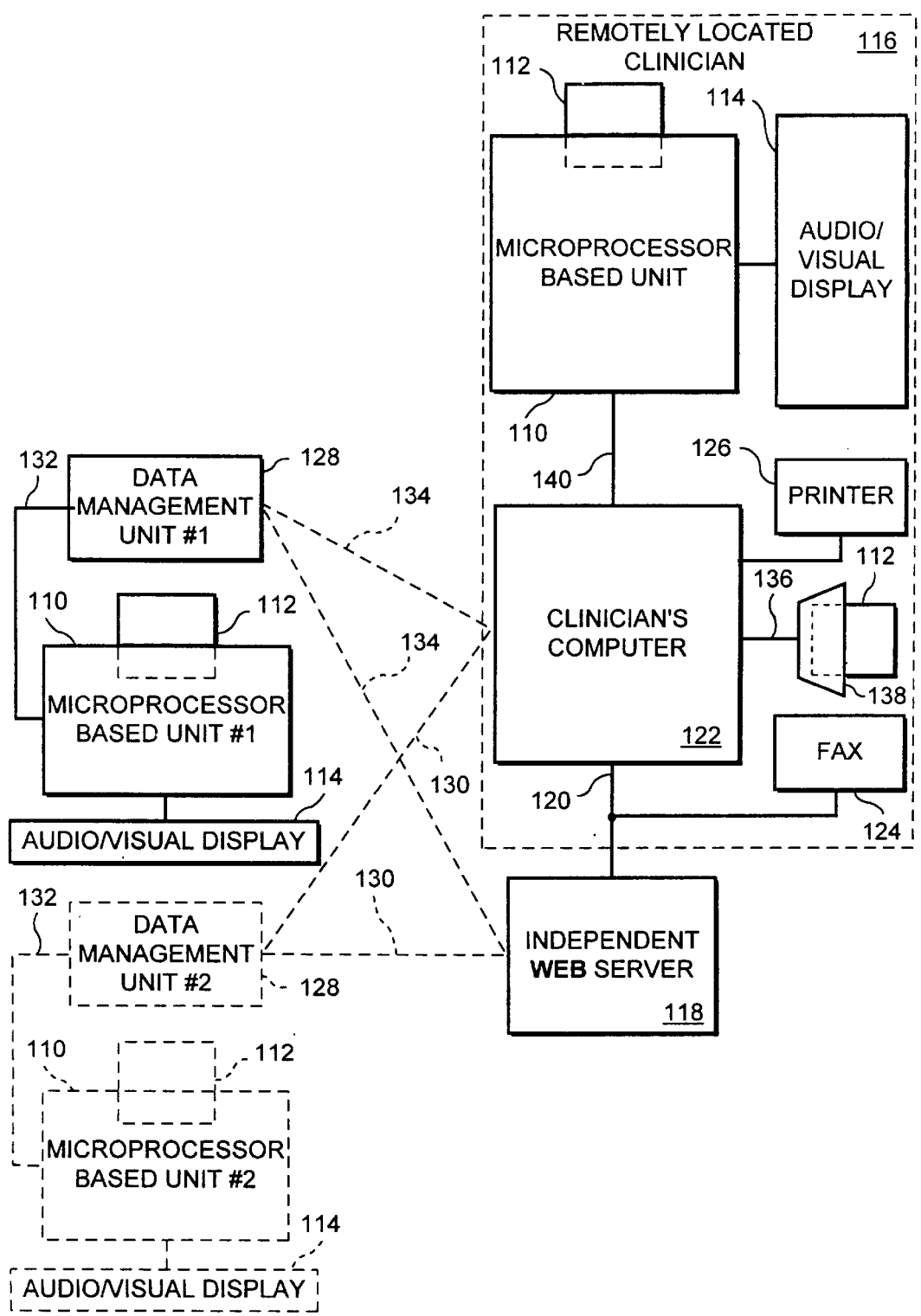
F I G. 3

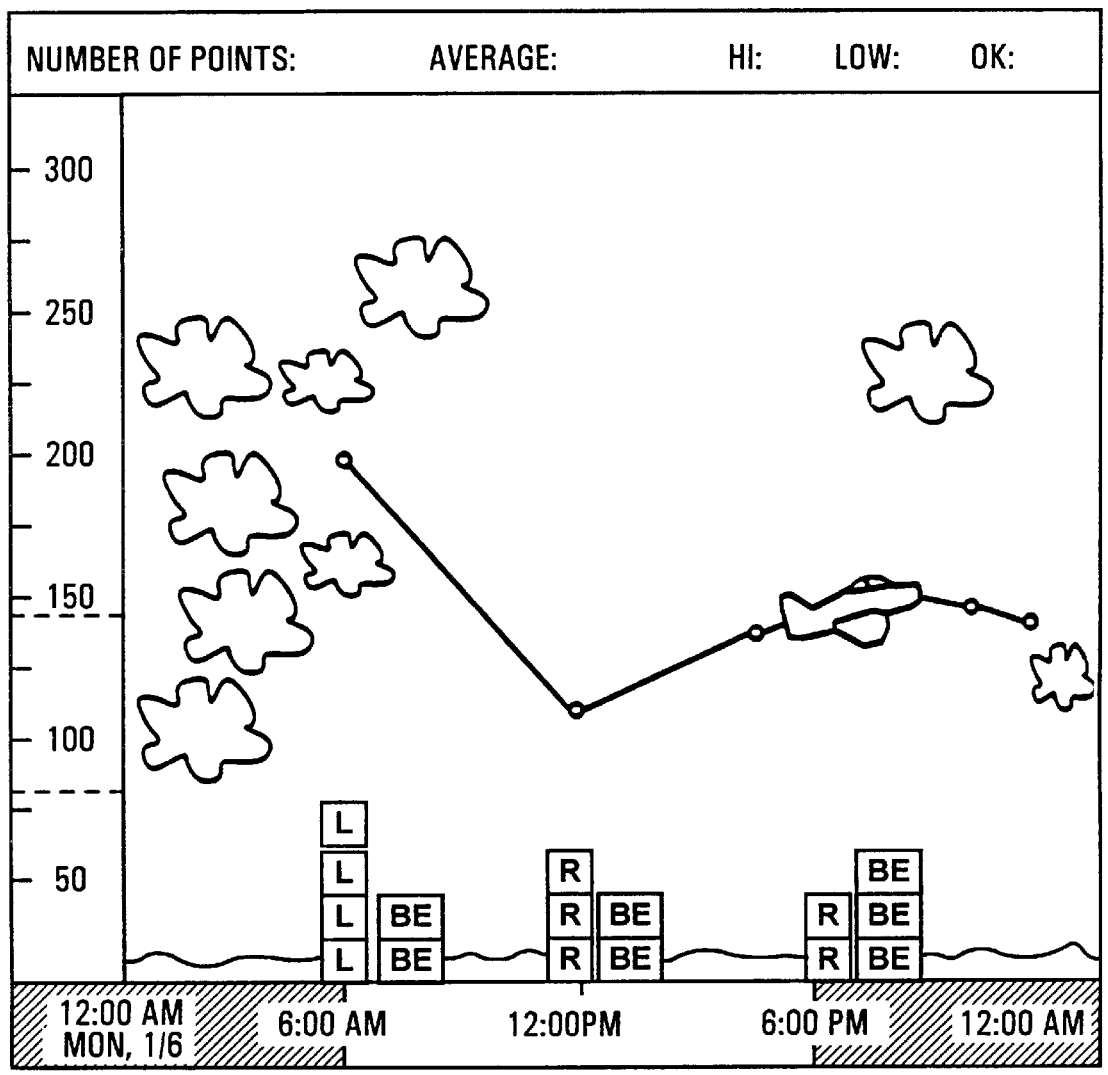
F I G. 8

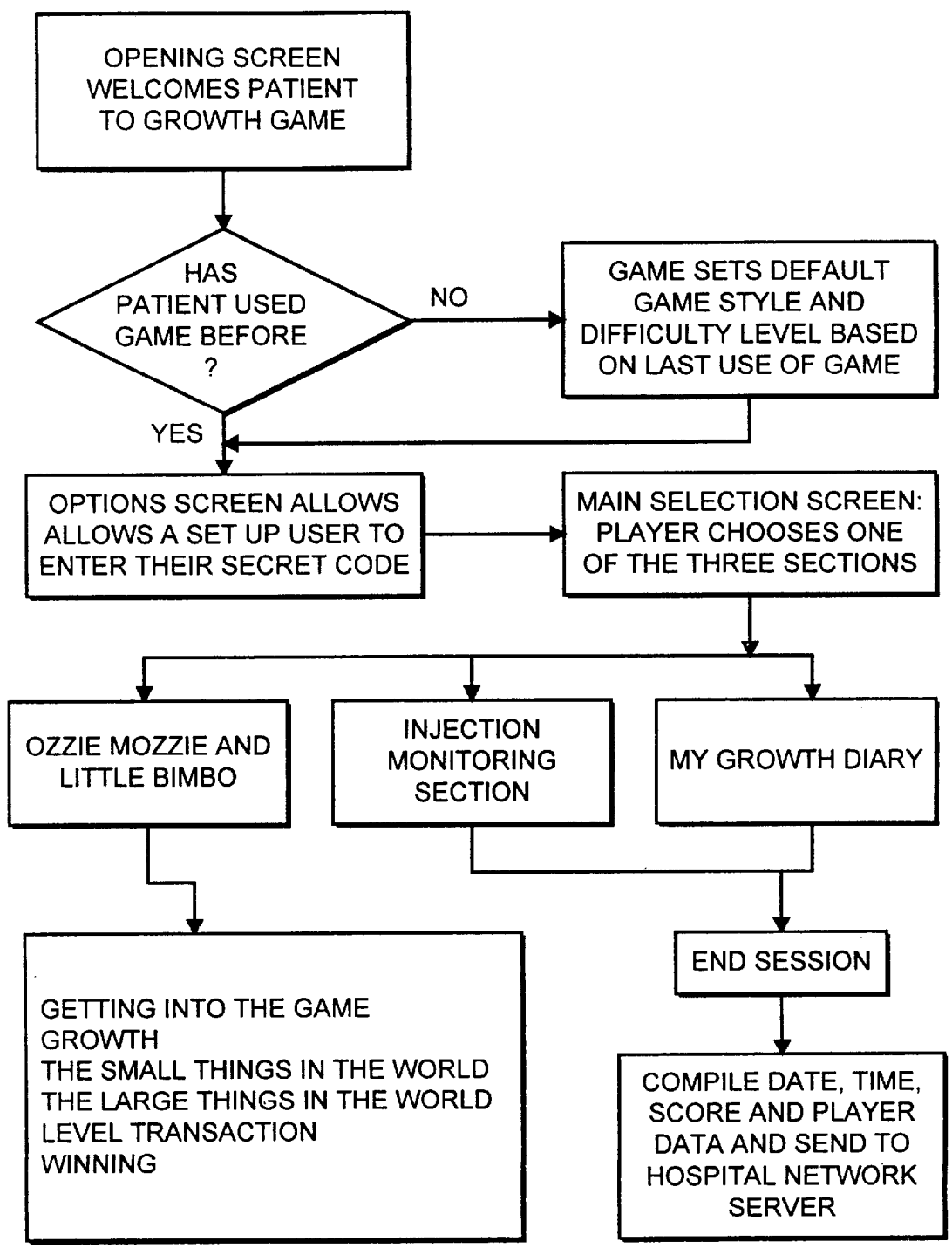
F I G. 13

METHOD FOR DIAGNOSIS AND TREATMENT OF PSYCHOLOGICAL AND EMOTIONAL CONDITIONS USING A MICROPROCESSOR-BASED VIRTUAL REALITY SIMULATOR

RELATED CASES

This is a continuation-in-part of application Ser. No. 08/958,786 filed Oct. 29, 1997, and U.S. Pat. No. 5,913,310 entitled "Method for Diagnosis and Treatment of Psychological and Emotional Conditions Using a Microprocessor-Based Video Game", which is a continuation-in-part of application Ser. No. 08/857,187 filed May 15, 1997, now U.S. Pat. No. 5,918,603, which is a continuation of application Ser. No. 08/247,716, filed May 23, 1994, now U.S. Pat. No. 5,678,571.

BACKGROUND—FIELD OF THE INVENTION

The present invention relates to methods and apparatus for diagnosis and treatment of psychological and/or emotional conditions in human patients with the aid of a microprocessor-based virtual reality simulator.

BACKGROUND—DESCRIPTION OF THE ART

A patient's behavioral response to his/her medical condition is evaluated and treated in conjunction with other, conventional therapy and is conducted by the primary physician, psychologist, psychiatrist, or other health care specialist. Depending on the medical condition, a preliminary picture of the patient's emotional condition may be available to the specialist in the form of answers to questionnaires or results from a battery of tests.

This type of evaluation is currently necessary in psychological conditions such as schizophrenia, depression, hyperactivity, phobias, panic attacks, anxiety, overeating and other emotional disorders or conditions wherein a patient's maladaptive behavioral response to his/her environment is the medical condition to be treated. Currently available tests for classifying such conditions rely on the patient to perform a self-examination and to respond candidly to a series of personal questions. Since most tests differ in their basic scientific assumptions, the results obtained are not standardized and cannot often be used to make meaningful case comparisons.

When applied to pediatric patients, problems existing in the art are amplified as compliance is not guaranteed and when the answering of questionnaires is aided by an adult, the input of the adult usually hampers rather than enhances objective responses. Cohen et al., *Am. J. Diseases of Children*, 143:1229–33 (1989). Self-evaluating questionnaires that allow a child to assess his or her own situation may provide a valuable comparison between the child's view of his or her behavior and that of adults, but the dependability of these questionnaires, especially in pre-adolescent children, has not yet been determined. Braswell et al., *Cognitive Behavioral Therapy with ADHD Children*, The Guilford Press, New York (1991). Currently available methods of psychological evaluation are painstaking and tedious, involve long hours of diagnostic evaluation and are, consequently, very expensive.

Following diagnosis, the actual therapeutic changes in the patient usually occur outside of the therapy sessions as cognitive and behavioral strategies learned in therapy are applied by the patient to problems encountered in day-to-day situations. Progress is predicated to a large extent on patient cooperation, discipline and the ability to self-manage. Lack of compliance to long-term therapy regimes presents a major obstacle to successful treatment. Children are a particularly difficult group of patients in this respect. Frequently, children lack the understanding, maturity and perseverance required to successfully pursue any kind of a treatment plan.

A patient, whether an adult or a child, may be experiencing any of a number of psychological conditions and/or disorders for which treatment is desired. Illustrative examples of disorders include schizophrenia, obsessive-compulsive disorder, dysthymic disorder, bipolar disorder, anxiety disorders, and impulse control disorders. Alternatively, the patient may be experiencing something that, while not considered to be a full-blown psychological disorder, is nevertheless a stressful, disturbing, and/or undesirable state of mind. For example, a child may experience separation anxiety when he or she starts attending school. A married couple, confronted with monetary or sexual problems, may seek marriage counseling. During divorce proceedings, psychological evaluations could be conducted to assist in determining custody arrangements. Victims of child abuse may require evaluation to determine an appropriate course of treatment.

A standard reference work entitled, "Diagnostic and Statistical Manual, Version IV", is widely utilized by psychiatrists, psychologists, and other mental health professionals to classify psychological conditions and disorders. This reference work, sometimes referred to as "DSM IV", is edited by the American Psychiatric Association. Unfortunately, the classification criteria tend to be classical categorizations, very academic in nature, and are often inapplicable or meaningless in the context of children and uneducated adults. Moreover, the DSM-IV is geared more towards the general classification of disorders and is not intended to provide an optimized treatment regime for a particular patient suffering from a specific condition.

By way of illustration, consider one fairly common psychological disorder: Attention Deficit Hyperactivity Disorder (ADHD). ADHD is characterized by the presence of any of the following indicia: inattention, impulsivity, hyperactivity, and boredom. As a practical matter, these indicia may manifest themselves as behavioral problems, social.maladjustment, aggression and/or academic difficulties. It is estimated that ADHD afflicts 3 to 5 percent of American children. Erickson, M., *Behavior Disorders of Children and Adolescents*, Prentice Hall, Englewood Cliffs, N.J. (1987); Barkley, R., *Attention Deficit Hyperactivity Disorder*, The Guilford Press, New York (1990). In many cases, ADHD significantly impairs performance at school. If left untreated, ADHD may continue into adulthood, creating problems at home and on the job.

Even with proper and early diagnosis, a reliable and consistently effective treatment for ADHD does not exist. In the United States, as many as 750,000 children take psychostimulant medication such as methylphenidate, dextroamphetamine or Ritalin® (CIBA Pharmaceuticals) every day to treat ADHD. Unfortunately, almost 25 percent of those children experience no behavioral improvement from such drugs, and almost half of the remaining children receive only marginal benefits. Greenhill, L., *Psychiatric Clin. of N. America*, 14:1–25 (1992). Although management techniques other than maintenance with psychostimulants exist, these techniques generally involve behavior therapy in combination with changes in family and school environments. But the implementation of these social changes is often a daunting task. Accordingly, a need exists in the art for techniques to assist in the diagnosis and/or treatment of ADHD by conveying assessment data to health care professionals. In this manner, these health care professionals could be better situated so as to monitor the progress of any ADHD treatment regime, and also to provide healing support. A need also exists in the art for techniques to assist in the diagnosis and treatment of the various sub-categories of ADHD, especially for those children who have ADHD but are not responsive to psychostimulants. These sub-categories of ADHD include (1) the primarily inattentive type; (2) the primarily impulsive-hyperactive type, and (3) the combined type.

Although the foregoing example illustrates the problems associated with diagnosing ADHD, these problems are also applicable in the context of other disorders and conditions, including but not limited to those specifically enumerated above. Thus, there also exists a need in the art for techniques designed to assist in the diagnosis and/or treatment of various psychological disorders and conditions. As in the case of ADHD, these disorders and conditions may also require extensive self-help and self-treatment. A patient may exhibit compulsive behavior, addictive substance abuse, gambling, smoking and/or alcoholism. At the present time, state-of-the-art treatment for these "medical" conditions involves counseling, distraction techniques and chemical replacement therapy. Ultimately, all of these methods depend upon the cooperation of the patient and require a large measure of self-motivation. This is especially important when the patient is in his or her own surroundings where the object(s) of the addiction or compulsion are easily accessible.

Some attempts have been made to use computers to diagnose and educate patients about their medical condition. Typically these attempts have produced questionnaires which can be filled out on a computer, or educational programs telling the patient more about his or her medical condition. Unfortunately, these projects stop short of being sufficiently adapted to patient needs, and a need exists in the art for a method and apparatus for diagnosis and treatment of psychological and/or emotional conditions in human patients with the aid of a microprocessor-based virtual reality simulator.

OBJECTS OF THE INVENTION

It is an object of the present invention to provide a method for monitoring, diagnosing and treating psychological disorders and/or conditions using a microprocessor-based system.

Another object of the invention is to provide methods for monitoring, diagnosing and treating psychological disorders such as schizophrenia, and behavioral disorders and/or conditions such as depression, hyperactivity, phobias, panic attacks, anxiety, overeating, obsessive-compulsive behaviors, addictions and substance abuse, using a microprocessor-based system.

A further object of the invention is to provide methods for diagnosing psychological disorders and conditions in children using a virtual reality simulation.

Yet another object is to provide a method and associated apparatus for diagnosis of psychological and emotional disorders in children using a virtual reality simulation.

Still another object is to provide methods and associated apparatus for the diagnosis of ADHD and sub-categories of ADHD, for those children who have ADHD but are not responsive to psychostimulants.

Another object is to provide a means for linking the inventive system to a network with a peripheral server capable of receiving, storing, processing, analyzing and exchanging data within the network.

These and other objects and advantages will become more apparent after consideration of the ensuing description and the accompanying drawings.

SUMMARY OF THE INVENTION

One aspect of the invention is a microprocessor-controlled virtual reality simulator adapted to receive commands generated by a user suffering a psychological disorder. The system generates complex multidimensional virtual reality display outputs to the user characterized by indicia configured and presented in a manner directed to aid in the diagnosis of the psychological disorder. The system comprises a control mechanism which uses a stored protocol directed to a specific psychological disorder and/or condition. The protocol is comprised of display controlling functions which include programming commands for presenting the display outputs in the form of one or more graphical elements on a display device. These graphical elements are representative of a three-dimensional virtual reality volume.

The diagnostic system also has an input mechanism for inputting user generated commands which are interactively entered in response to the virtual reality display outputs, and an output mechanism for relaying a series of diagnostic outputs to a health care professional such as a physician or nurse. The series of diagnostic outputs are configured so as to provide a presentation of the user's inputs to the health care professional to aid in the diagnosis of the psychological disorder and/or condition presented by the patient.

In the diagnostic system, the protocol of display controlling functions includes programming commands for manipulating at least one graphical character presented on the display. The stored protocol is specifically configured to provide a test battery of continuous performance tasks through displays to the user, and can further comprise a data collection subsystem for storing and analyzing the user's inputs responsive to the test battery, and for relaying the analytic results via the series of diagnostic outputs to the health care professional for diagnosing the psychological disorder.

The system can further comprise an interfacing mechanism for linking the system to a network. The interfacing mechanism may comprise a device for interfacing the microprocessor to the network, and also to at least one peripheral server linked to the network. This server is adapted to receive the inputted user generated commands and the diagnostic outputs, and is also adapted to exchange data within the network. The server may include a receiver, a memory device, and a mechanism for processing the inputted user generated commands and the diagnostic outputs. The network server may include an optional second microprocessor-controlled data processing unit in communication with the system. This second microprocessor controlled data processing unit is adapted to process and exchange data with the system.

The psychological disorders and/or conditions contemplated herein may include, by way of illustration but not limitation, obsessive-compulsive disorder, the impulse control disorders (anger control problems, intermittent-explosive disorder), dysthymic disorder, bipolar disorder, narcissistic personality disorder, ADHD, schizophrenia, depression, hyperactivity, phobias, panic attacks, anxiety, overeating, compulsive behaviors, addictions and substance abuse. However, this is not a comprehensive list, and those skilled in this art and the medical arts could easily adapt the disclosed invention to other similar disorders and/or conditions. Moreover, the invention is also applicable to psychological evaluations in the context of marital counseling, child custody arrangements, separation anxiety, pain management, child abuse investigations, and other potentially stressful situations.

Optionally, the invention may also provide for the administration of one or more disorder or condition-specific tests. By way of illustration, when the patient presents symptoms tending to indicate a diagnosis of ADHD, these tests may include auditory and visual delayed reaction time tests for attention. The system may comprise an administrator program for configuring these tests.

Another aspect of the invention is a method for diagnosing a psychological disorder in a human patient. For one or more disorders and/or conditions, electronic instructions are provided that represent an interactive virtual reality simulation configured for that psychological disorder and/or condition. The electronic instructions are executed on a microprocessor-based system adapted to receive input data from a patient, and also adapted to provide an interactive three-dimensional display to the patient. This system further includes memory device that stores a protocol directed to diagnosis criteria for one or more psychological disorders and/or conditions. Next, the electronic instructions are loaded into the microprocessor-based system, and the human patient may optionally be instructed on how to use the microprocessor-based unit to play the virtual reality simulation. The inputted data from the patient are collected and analyzed, based on the protocol, to arrive at the diagnosis. The method can include analysis of the input data from the patient to categorize whether or not the patient is responsive to maintenance psychostimulants.

The invention may also encompass a microprocessor-controlled virtual reality simulator directed to the treatment of a psychological disorder. The treatment system comprises a controlling mechanism for controlling the system using a stored protocol directed to the psychological disorder in question, comprised of display controlling functions wherein the functions include programming commands for controlling one or more three-dimensional graphical elements presented on a display. The treatment system also has an input mechanism for inputting user generated commands which are interactively entered by the user in response to display outputs presented on a multidimensional display mechanism. The system also includes an interpreting mechanism for interpreting the inputted user generated commands, then applying the stored protocols to the inputted commands, and based thereon, controlling the output to the display wherein the output is specifically configured to provide a presentation to the user that enhances the treatment of the psychological disorder. In the therapeutic system, the stored protocol can also be configured to provide experiential education specific to the psychological disorder. For example, consider a therapeutic system based on treatment for ADHD. The stored protocol may then be configured to provide opportunities to practice activities such as "focus of attention" and "impulse control" while, at the same time, providing supportive and performance feedback, and general information about ADHD and its treatment.

Also provided is a method for treatment of a psychological disorder in a human patient which initiates with providing the patient with a microprocessor controlled virtual reality simulator capable of interacting with the patient to obtain personal data related to the psychological disorder. The obtained personal data is transmitted to another microprocessor controlled system capable of collecting and analyzing the data. A compiled report based on the collected and analyzed data is automatically generated by the system and criteria specific to the patient are generated to implement a optimum treatment regimen for the psychological disorder. When dealing with ADHD, the treatment regimen includes management of psychostimulant medication.

The invention also encompasses a method for monitoring a psychological disorder in a human patient comprising the steps of encoding electronic instructions for an interactive virtual reality simulation configured for the psychological disorder to be monitored. The simulation comprises a microprocessor controlled system capable of receiving input data from and providing a multidimensional interactive display to the patient. The system further comprises a stored protocol directed to criteria for monitoring the specific psychological disorder of the patient. The monitoring method further comprises the steps of loading the electronic instructions into the microprocessor-based system, instructing the patient on how to use the microprocessor-based unit to play the interactive virtual reality simulation, and monitoring input data from the patient. The stored protocol is specifically configured to provide a test battery of continuous performance tasks to the patient through the interactive display, and the input data from the patient in response to the test battery is monitored to facilitate diagnoses and treatment of the psychological disorder.

BRIEF DESCRIPTION OF THE DRAWINGS

FIG. 3 is a block diagram that illustrates microprocessor-based patient units connected in signal communication with a clinician's computer system and/or an independent web server through the internet, for collection and analysis of diagnostic data originating with a large number of patient units.

FIGS. 8, 9 and 10 are exemplary screens of a virtual reality simulation for self-treatment of diabetes.

FIG. 13 is a flowchart for the Growth virtual reality simulation.

DETAILED DESCRIPTION OF THE INVENTION

Figure 1:
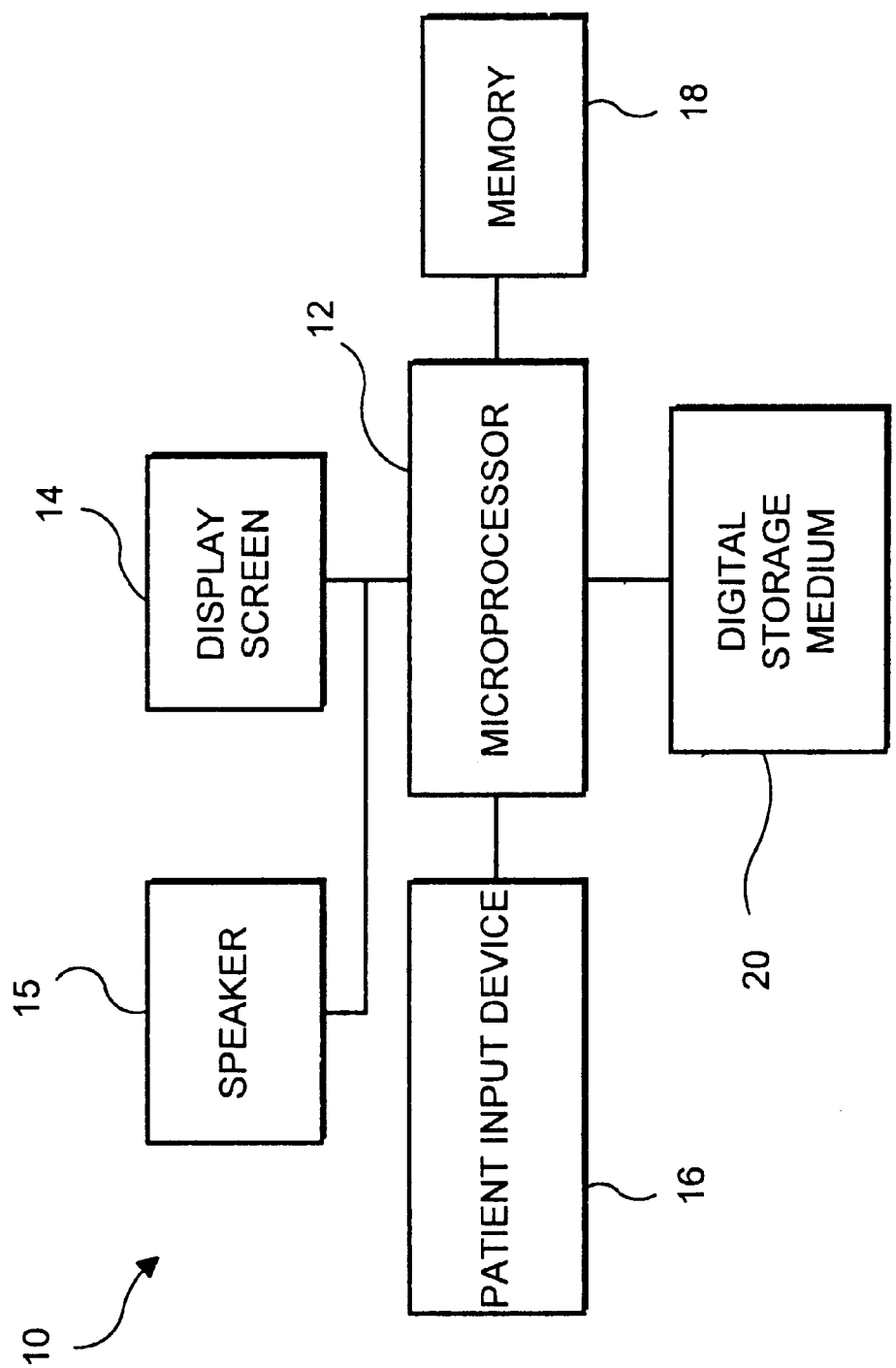
FIG. 1 is a block diagram depicting the apparatus system employed in the method according to the invention.

FIG. 1 shows a block diagram representing a typical embodiment of a computer or microprocessor-based unit 10 capable of supporting virtual reality simulations for patient treatment. At the heart of unit 10 is a microprocessor 12. In addition to operations necessary to run unit 10, microprocessor 12 can process multidimensional video data representative of a space having at least three dimensions. In more complicated systems, the tasks of microprocessor 12 can be performed by a number of microprocessors.

A virtual reality display headset or screen 14 is connected to microprocessor 12. The resolution and size of display screen 14 are sufficient to project multidimensional visual images generated by virtual reality simulations. Screen 14 can be a high-resolution video screen mounted within a headset or helmet that at least partially encircles the head of the wearer. A speaker 15 for producing virtual reality sounds is hooked up to microprocessor 12 as well.

A patient input device 16 is also connected to microprocessor 12. Input device 16 can be a keyboard, joystick, mouse, button, trigger, light-pen, simulated human hand, tracking ball, or the like, or combinations of these devices. A suitable choice of input device 16 is made based on the virtual reality simulation displayed on display screen 14 and the medical conditions of the human patient. The selected input device 16 will thus permit the patient to actively participate in the virtual reality simulation.

Additionally, microprocessor-based unit 10 has a memory 18, which is in communication with microprocessor 12. Memory 18 contains data used by microprocessor 12 to operate unit 10. While in the exemplary embodiment illustrated in FIG. 1, memory 18 consists of a single unit, configurations with a plurality of memory units, and/or memory units of different types, are possible.

Unit 10 is also coupled to a digital storage medium 20 and appropriate data reading devices (not shown). Digital storage medium 20 can represent, for example, a hard-disk, a floppy disk, a compact disk (CD), a cartridge, a network storage unit, a mechanism for sending signals over a network, a carrier wave, an electromagnetic wave, or any other entity capable of storing and/or conveying electronic instructions for running a virtual reality simulation on unit 10. The ability to store and/or convey a large amount of data is desirable in the context of virtual reality simulations.

Figure 2:
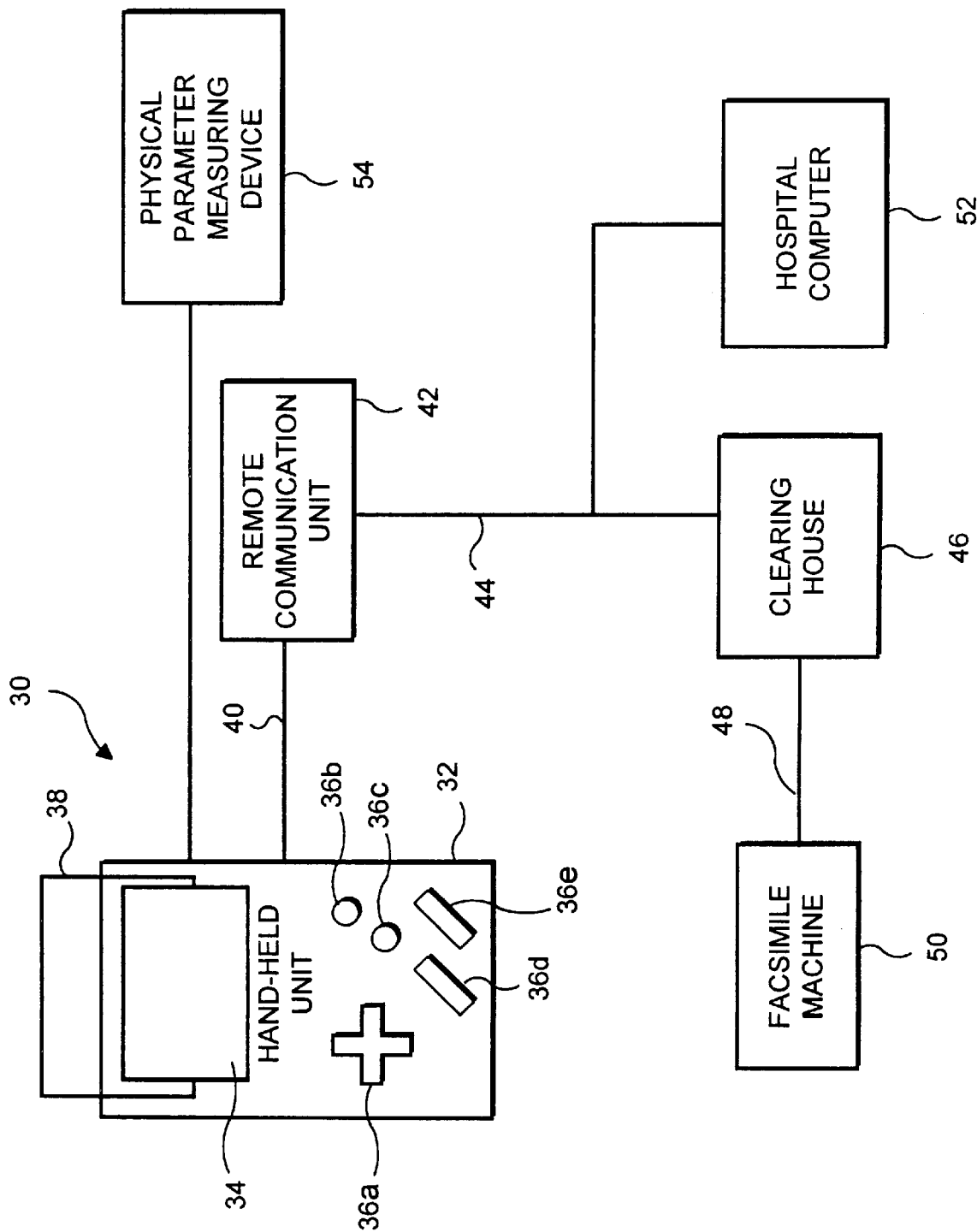
FIG. 2 is a block diagram of a system employing a handheld microprocessor unit for implementing the method and system of the present invention.

The block diagram of FIG. 2 shows a particularly convenient embodiment for implementing the diagnosis and treatment method. A hand-held microprocessor unit 30 is equipped with a video display 34 capable of displaying three-dimensional simulations and a number of input switches or keys 36a, 36b, 36c, 36d and 36e, which are mounted on a housing 32. A set of components including a microprocessor, memory circuits and circuitry that interfaces keys 36a, 36b, 36c 36d and 36e with the microprocessor is installed inside housing 30 but not shown in FIG. 2. Stored in the memory of programmable hand-held microprocessor unit 30 is a set of electronically encoded program instructions. These instructions establish a data protocol that allows hand-held micro-processor unit 30 to perform digital data signal processing and generate desired data or graphics for display on display unit 34 when a program cartridge 38 is inserted into a slot or other receptacle in housing 32. That is, cartridge 38 of FIG. 2 includes read-only memory data encoding the instructions for activating a particular virtual reality simulation.

Illustrative implementations for the hand-held microprocessor unit 30 include laptop computers and palm pilots. Hand-held microprocessor unit 30 may be hooked up to a remote communication unit 42 via a connection cable 40. Preferably unit 42 can be a modem capable of communicating over telephone lines, or a radio-frequency transceiver adapted for wireless communication of information. Other telecommunications devices known to the art can also be used. By way of example, the embodiment shown in FIG. 2 utilizes a high-speed modem unit 42.

A communication line 44, in this event a telephone line, connects unit 42 to a data clearing house 46 and hospital computer 52. This set-up establishes an efficient data pathway from hand-held microprocessor unit 30 to clearing house 46 and hospital computer 52. Clearing house 46 is capable of classifying data and sending appropriate messages concerning the patient's medical condition to a health care professional or physician. In the preferred embodiment, clearing house 46 is connected by transmission line to a facsimile machine 50 standing in the office of a physician or health care professional.

A physical parameter measuring device 54, such as a glucose blood meter or a respiratory flow meter, is also connected to hand-held unit 30. Device 54 is designed for patient self-monitoring while engaged in a virtual reality simulation. For this purpose device 54 is capable of downloading measurement data into hand-held microprocessor unit 30. Appropriate choice of device 54 is made by the physician, possibly depending on other system hardware and/or the intended virtual reality simulation to be used for patient treatment.

FIG. 3 illustrates one embodiment of a diagnostic measurement system configured in accordance with the invention. The depicted embodiment includes a programmable microprocessor-based unit 110 that includes a receptacle for receiving an external memory unit 112, which can be easily inserted and removed from microprocessor-based unit 110. Removable memory unit 112 includes a digital storage medium for storing program instructions that control the operation of microprocessor-based unit 110 and, in addition, allows storage of diagnostic test information that is generated during operation of microprocessor-based unit 110 for diagnostic assessment of a psychological condition.

Various storage media known to those skilled in the art can be used as the digital storage medium of external memory unit 112. For example, conventional read-only memory (ROM) can be employed for storage of program instructions that are not changed or altered when external memory 112 is reconfigured for a different patient or reconfigured for measurements relating to a different type of psychological condition. Optically-scannable memory, such as currently-available compact disc memory, can also be employed. In addition, various types of erasable read-only memory and random access memory (RAM) having a battery back-up can be used to provide a storage medium for program instructions that may be changed when external memory 112 is configured for use with a different patient or for the diagnostic assessment of a different psychological condition. Erasable read-only memory or battery backed-up RAM also can be used for storage of information gathered when microprocessor-based unit 110 is operated to gather diagnostic measurement information that relates to one or more psychological conditions. Moreover, in newly developing technologies such as audio/video interactive television and networks for digital communications, program instructions can be transmitted over interactive links to microprocessor-based unit 10 and stored in random access memory.

As is indicated in FIG. 3, microprocessor-based unit 110 is interconnected with an audio/visual display unit 114 equipped to display visual representatives in three or more dimensions. During operation of the invention for diagnostic assessment of psychological conditions, microprocessor-based unit 110 generates audio and video signals that are presented to the patient or system user by audio/visual display unit 114. The audio/visual presentation is controlled by program instructions that are either stored in external memory 112 or are otherwise supplied to microprocessor-based unit 110. In the disclosed embodiments, the visual presentation is structured in the form of a virtual reality simulation to elicit responses from the user of microprocessor-based unit 110, (e.g., a patient or research subject) so as to provide diagnostic measures relating to a particular psychological condition.

In that regard, one preferred embodiment disclosed herein is arranged for diagnostic assessment of Attention Deficit Hyperactivity Disorder (ADHD). Upon understanding the operation of the invention and the various manners in which it can be configured, it will be recognized that the invention can be used in the diagnoses of various other psychological conditions and behavior patterns, including anxiety disorders, depression, schizophrenia, addiction, weight control disorders, the disorders and conditions mentioned in the Background of the Invention, and various other psychological disorders and/or conditions as well.

A primary advantage of the invention is the ability to conduct diagnostic assessment procedures in environments other than a clinician's office or a health care facility. This particular aspect of the invention can be important with respect to diagnosing psychological conditions that are highly situation-dependent. Further, since it is not necessary for a clinician to be present when a diagnostic assessment procedure is executed, the costs of diagnosis and treatment are reduced. For example, during a clinical session, a clinician can instruct a patient or subject in the use of the invention for diagnostic assessment of a particular psychological condition. The patient or user then uses microprocessor-based unit 110, a suitably programmed external memory unit 112, and a multidimensional audio/visual display unit 114 between clinical sessions to gather appropriate diagnostic measurements while the subject is in suitable environmental surroundings (e.g., at home, school, or the workplace). Information gathered during the diagnostic assessment is then made available to the clinician for consideration and analysis.

There are two basic techniques by which information that relates to the results of a diagnostic assessment can be conveyed to a clinician or other person who serves as an administrator for the conduct of the diagnostic assessment. These same techniques are employed for establishing the diagnostic procedure (i.e., storing suitable program instructions in external memory unit 112). The first technique for transferring test results, and/or for programming microprocessor-based unit 110/external memory unit 112, involves data transmission between processor-based unit 110 and a remotely located clinician's office (or other health care facility). Another technique for transferring test results and/or programming utilizes a remotely-situated facility that stores test results for subsequent analysis and transmission to the clinician. Pursuant to this second technique, microprocessor-based unit 110 (or external memory unit 112) is physically transferred between the site at which the diagnostic assessment is made and the clinician's facility or other remote location.

With respect to the first information transfer technique, FIG. 3 schematically illustrates an arrangement of the invention for remote exchange of data and information between a microprocessor-based unit 110 and either a remotely located clinician 116 or, for example, a web server 118 through the internet which is independent of the clinician. In such an arrangement, independent web server 118 includes one or more digital signal processors sufficient for gathering diagnostic measurement information from a relatively large number of microprocessor-based diagnostic tools represented by microprocessor-based unit 110 and microprocessor-based unit #2 of FIG. 3.

A communications link 120 is shown in FIG. 3 between independent web server 118 and the clinician's remote location 116 to indicate a transfer of information electronically and/or by other signal transmission means. Communications link 120 represents any of various ways of communicating information with and/or without the use of wires. For example, in some instances, communications link 120 may represent a signal path established by a telephone system. In other instances, communications link 120 may be implemented using wireless technology, for example, in the form of an RF transceiver. Moreover, a combination of RF transceivers, telephone lines, and/or modems can be utilized. Communications link 120 may also be established through the use of specialized digital networks, including those provided by interactive audio/video systems that operate using cable television, fiber optic cable, and/or RF communication links. Communications link 120 may be equpped to transfer data and information between web server 118 and a clinician by various conventional data transmission systems, including those implemented through the internet such as via HTTP, TCP/IP, and/or others.

As is indicated in FIG. 3, the signals sent by web server 118 to the clinician's facility 116 can be coupled to devices such as the clinician's computer 122 and/or the clincian's facsimile machine 124. Signals transmitted to the clinician's computer 122 can be stored with or without additional processing.

In the same regard, analytical signal processing of the diagnostic assessment data gathered by microprocessor-based unit can be performed at various stages of information transmission between patient and clinician. For example, data processing can be performed in the microprocessor-based unit 110, the clinician's computer 122, web server 118 and/or a data management unit 128 to be described below. In any case, when the diagnostic information is transmitted to the clinician's facility, it can be displayed on a display unit of the clinician's computer 122, printed by a printer 126 that is connected to computer 122, or processed by other devices that are peripheral to the clinician's computer 122. It is to be noted that the clinicians computer 122 at facility 116 can itself be programmed to be a web server with proper hardware configurations, as will likely be more practical with large numbers of patients and for multi-clinician-based hospitals.

With continued reference to the embodiment of the invention shown in FIG. 3, signals representative of information gathered during a diagnostic assessment procedure (and other signals appropriate to system operation) are coupled to (or from) independent web server 118 and the microprocessor-based unit 110 via a data management unit 128 and a communications link 130. As was the case with communications link 120, which provides for the transfer of information between web server 118 and the clinician's facility 116, communications link 130 may represent any of various ways of communicating information with and/or without the use of wires. For example, in some instances, communications link 130 may represent a signal path established by a telephone system. In other instances, communications link 130 may be implemented using wireless technology, for example, in the form of an RF transceiver. Moreover, a combination of RF transceivers, telephone lines, and/or modems can be utilized. Communications link 130 may also be established through the use of specialized digital networks, including those provided by interactive audio/video systems that operate using cable television, fiber optic cable, and/or RF communication links. Communications link 130 may be equpped to transfer data and information between web server 118 and a clinician by various conventional data transmission systems, including those implemented through the internet such as via HTTP, TCP/IP, and/or others.

In the arrangement of FIG. 3, data management unit 128 can be interconnected with its associated microprocessor-based unit 110 by a communications link which, for purposes of illustration, is shown as a cable 132. However, it is to be understood that a hard-wired cable is not required, as the interconnection could also be accomplished as described above in connection with communication links 120 and 130. In the illustrative example of FIG. 3, cable 132 includes electrical conductors and/or fiber optic cable for carrying signals between the two units. Of course, this cable could be replaced by an IR (infrared) communications link, and/or a wireless communications link, and/or some other type of data communications link. Data management unit 128 provides the signal processing that is necessary for interfacing microprocessor-based unit 110 with communications link 130 and/or a communications link 134. Communications link 134 provides for transmission of signals between microprocessor-based unit 110-and the clinician's remote location 116 (e.g. coupling of signals to and from the clinician's computer 122). As in the case of the previously discussed communications links 120 and 130, communications link 134 can be implemented in any of a variety of ways.

Owing to the wide variety of hardware and software that can be used to implement communications links 130 and 134, data management unit 128 may take on any of various forms and configurations. For example, if communications link 130 and/or 134 represents a signal path established by a conventional telephone system, data management unit 128 will include a modem and will operate to perform the signal processing necessary to transmit information to independent web server 118 and/or the clinician's remote location 116. In some arrangements of the invention, the signal processing required for modem data transmission will be implemented by a microprocessor unit that is incorporated in data management unit 128. In other situations, the microprocessor of processor-based unit 110 can be employed to perform the signal processing necessary for modem signal transmission. Similarly, the hardware associated with modem transmission (e.g. telephone line connection) can be included in data management unit 128 or incorporated in microprocessor-based unit 110.

FIG. 3 also indicates one manner in which the invention can be employed for remote administration of diagnostic assessment of psychological conditions without the need for data management unit 128 and communications links 130 and 134. In particular, in the arrangement of FIG. 3, an external memory unit 112 can be inserted in a receptacle 138 that electrically connects external memory unit 112 to the clinicians' computer 122 via a cable 136. With an external memory 112 connected in this manner, a clinician or other administrator of the diagnostic assessment to be performed can operate computer 122 to store program instructions appropriate for the diagnostic procedure in an external memory unit 112. The programmed external memory unit 112 can be given to a patient or subject at the end of a clinical session or transmitted to the patient or subject by other appropriate means. The patient or subject can subsequently insert the programmed external memory unit 112 in a microprocessor-based unit 110 that is located at the patient's home or some other location at which the virtual reality simulation will be executed. Signals representative of the diagnostic information gathered during the virtual reality simulation are stored in external memory unit 112 when microprocessor unit 110 implements the diagnostic assessment procedure. External memory unit 112 is then returned to the clinician, inserted into receptacle 138 and the clinician's computer 122 is used to retrieve the diagnostic information stored in the external memory unit 112. In situations in which program instructions and diagnostic results are stored internally in microprocessor-based unit 110 (i.e. without use of an external memory unit 112), the entire microprocessor-based unit can be taken to the clinician's office. Information relating to diagnostic assessment results can then be unloaded to the clinician's computer 122 and, if desired, program instructions can be downloaded to the microprocessor-based unit 110 for administering further diagnostic assessment.

As also is shown in FIG. 3, in most applications of the invention, an additional microprocessor-based unit 110 and multidimensional audio/visual display unit 114 will be located at the clinician's office or other facility. In the arrangement shown in FIG. 3, the additional microprocessor-based unit 110 is directly connected to the clinician's computer 122 by an electrical cable 140 to allow signal transmission between the microprocessor-based unit and computer 122. Providing a microprocessor-based unit 110 and multi-dimensional audio/visual display unit 114 at the clinician's location allows a patient or subject to be instructed in the use of the system and also allows the administration of diagnostic assessment procedures at the clinician's facility, if desired.

Figure 4:
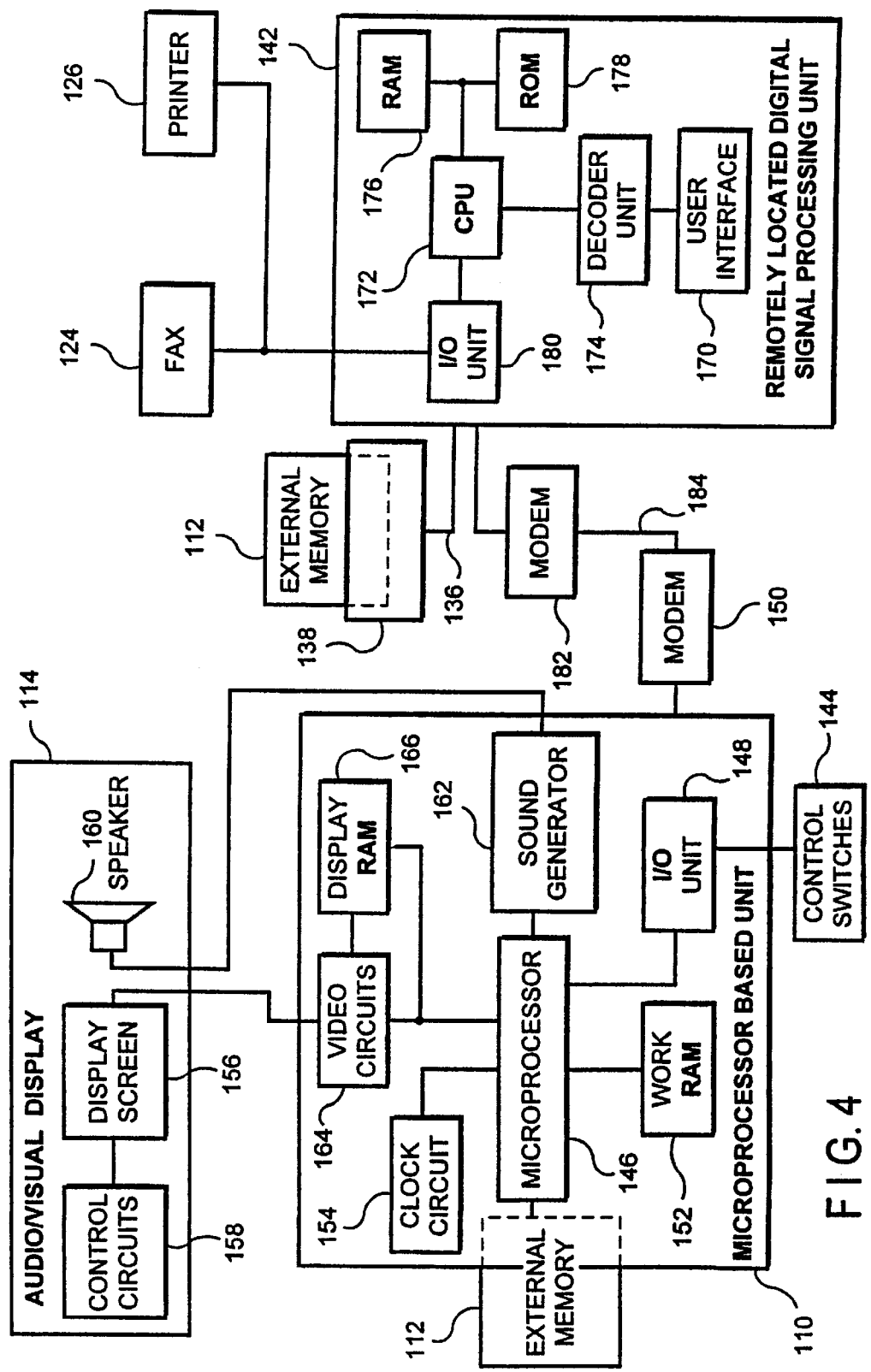
FIG. 4 is a block diagram illustrating in greater detail the basic structure of a microprocessor-based patient unit and a digital signal processor of a type that can be used by the clinician's PC, an intranet at the clinician's site or by an independent web server.

FIG. 4 depicts a detailed block diagram of a microprocessor-based unit 110 that can be employed in the practice of the invention and an associated multidimensional audio/visual display unit 114. Also shown in FIG. 4 is a basic block diagram of a remotely located digital signal processing system 142 which typifies the arrangement of web server 118 and computer 122 of FIG. 3. As is indicated in FIG. 4, signals supplied by one or more control switches 144 are coupled to a microprocessor 146 of microprocessor-based unit 110 via an input/output circuit 148. Also interconnected with input/output unit 148 of microprocessor-based unit 110 is an external modem 150, which serves as data management unit 148 (FIG. 3) for the depicted arrangement. Although not indicated in FIG. 4, it will be understood by those skilled in the art that interconnections such as the connection shown between microprocessor 146 and input/output unit 148, generally include a data, address, and control bus.

With continued reference to microprocessor-based unit 110 of FIG. 4, microprocessor 146 is interconnected with the receptacle that receives an external memory unit 112 so that microprocessor 146 can access virtual reality simulation program instructions stored in external memory unit 112 and store diagnostic assessment results in external memory 112. As previously mentioned, virtual reality simulation program instructions can be provided to a microprocessor-based unit 110 via a digital signal communications system, instead of an external memory unit 112. In such arrangements, digital signals supplied by a system such as cable television or a digital communications can be coupled to microprocessor 146 via input/output unit 148 or other conventional signal processing arrangements.

In the arrangement of FIG. 4, a random access memory 152 is interconnected with and is used by microprocessor 146 to implement a desired virtual reality simulation for purposes of diagnostic assessment and to perform any desired analysis of the gathered diagnostic data. In addition, random access memory 152 can be used for storing program instructions that are supplied to any embodiments of the invention that do not employ an external memory unit 112 (i.e. embodiments in which program instructions are supplied via a digital signal communications system). A clock circuit 154 is provided to allow microprocessor 146 to store date and time signals in situations in which date and time tags are to be included with the gathered diagnostic data. Although not specifically shown in FIG. 4, microprocessor-based unit 110 may include an internal read-only memory for storing various program instructions and data that are not necessarily unique to a particular virtual reality simulation or other application for the microprocessor-based unit 110.

The multidimensional audio/visual display unit 114 that is shown in FIG. 4 corresponds to a video display system that includes control circuitry 158, a speaker 160, and either or both of a holographic device and one or more display screens 156. These display screens 156 and/or holographic projection devices may, but need not, be incorporated into a helmet which fits over or next to a patient's head. In an arrangement of this type, microprocessor 146 of microprocessor-based unit 110 controls the operation of a sound generator 162 and video circuits 164 in accordance with the program instructions stored in external memory 112. A display random access memory 166 is used to store and format video signals which are coupled to display screens 156 and/or holographic projection devices of audio/visual display unit 114. Music, synthesized speech, and other sounds generated by sound generator 162 are coupled to speaker 160. Control circuit 158 includes the circuitry necessary for adjusting volume and display quality as well as the circuitry for driving the display unit 114. In other arrangements, a television set may be used as part of the audio/visual display unit 114 and/or for speaker 160, with microprocessor-based unit 110 supplying an appropriate modulated rf signal or being connected to the television set video and/or audio inputs.

It will be recognized by those of skill in the art that a diagnostic tool that corresponds to microprocessor-based unit 110 of FIGS. 3 and 4 can be realized using conventional microprocessor design techniques and components. It also will be recognized that various commercially available devices can be adopted for use as a microprocessor-based unit 110 of this invention. In that regard, in the currently preferred embodiments of the invention, the microprocessor-based unit 110 is a virtual reality, multidimensional video system, with external memory unit 112 being configured to correspond to the type of virtual reality simulation that is used with that particular video system.

Virtual reality simulations are simple and intuitive to use. Therefore, little time is required for instructing a patient or other system user in how to operate the simulation for performance of a particular diagnostic assessment. Even further, a virtual reality simulation provides a convenient way for realizing diagnostic assessment procedures that are presented in game-like or fantasy-like format with animation or other graphics that provide motivation for all age groups while gathering needed diagnostic data. The cumulative effect is achievement of an unobtrusive test and diagnosis arrangement that is acceptable to patients and other subjects and can be used in many environments.

Referring again to FIG. 4, the remotely located digital signal processing unit 142 may correspond to any of a wide range of computational arrangements, including the clinician's computer 122 and the previously discussed, more complex, web server 118 of FIG. 3. In the arrangement depicted in FIG. 4, a user interface 170 is connected in signal communication with a central processor unit 172 via a decoder circuit 174. Random access memory 176 and read-only memory 178 can be accessed by central processor unit 172 of digital signal processing unit 142 during execution of the various programs and procedures used in carrying out the invention. An input/output unit 180 acts under the direction of central processor unit 172 to provide signals to a facsimile unit 124 and printer 126. As also is indicated in FIG. 4, signals can be provided to central processor unit 172 via input/output unit 180 by a modem 182. In the arrangement shown, a communication link 184 interconnects modem 182 with modem 150, thus permitting the digital signal processing system to receive diagnostic test information from the microprocessor-based unit 110. Input/output unit 180 can be connected to a receptacle 138, which, as was described in the context of FIG. 3, allows the digital data processing system to access storage addresses within an external memory unit 112 that is connected to receptacle 138.

As shall be described in more detail, an administration program that is executable by digital signal processing unit 142 includes a program module that allows program instructions to be stored in an external memory unit 112 to establish a desired diagnostic assessment procedure. Execution of another module of the administration program by digital signal processing unit 142 allows the retrieval of diagnostic test data stored in external memory unit 112 when a diagnostic assessment procedure was conducted (i.e. when a patient or user executed a virtual reality simulation in accordance with a desired diagnostic procedure).

One currently-preferred embodiment of the invention is directed to the diagnostic assessment of a psychological condition or disorder. The specific virtual reality simluation or simulations to be executed by the microprocessor-based unit 110 depend upon the particular disorder and/or condition to be diagnosed. Assume, for purposes of illustration, that attention deficit hyperactivity disorder (ADHD) is to be diagnosed, although it is to be clearly understood that other types of psychological conditions and/or disorders could be evaluated instead. In the case of ADHD, a set of program instructions are provided to the microprocessor-based unit. These instructions provide virtual reality simulations that effectively perform one or more tests that assess various aspects of an ADHD patient's attention. These program instructions are stored in external memory unit 112. Two basic types of tests are employed—(1) virtual reality tests that include a series of delayed reaction tasks, and (2) virtual reality tests that include a series of continuous performance tasks. In the delayed reaction tasks, programmable microprocessor-based unit 110 operates to generate an audible and/or multidimensional visual warning signal to alert the user—i.e., the patient—that the microprocessor-based unit soon will produce an audible and/or visual trigger stimulus. When the trigger stimulus is generated, the patient and/or user activates a designated switch or control of microprocessor-based unit 110 (e.g., a switch, control, or transducer included in control switches 144 of FIG. 4). This designated switch or control may represent one or more predefined objects or entities of the virtual reality simulation.

In current practice, the clinician or other administrator of the virtual reality simulation can select one or more audio delayed reaction tests and/one or more video delayed reaction tests when establishing a battery of virtual reality simulation tests for a particular patient or user. As shall be described in more detail below, the clinician establishes the battery of tests by executing a computer program, which also allows the clinician or administrator to establish the sequence in which various virtual reality simulation tests will be administered and, for each audio or visual delayed reaction test, select both the number of virtual reality trigger stimuli to be generated and a time delay range. The time delay range establishes the upper and lower bounds of the delay between virtual reality warning stimuli and virtual reality trigger stimuli. The specific delay between a particular warning stimulus and its associated trigger stimulus is selected randomly by microprocessor-based unit 110 when the delayed reaction test is conducted.

Each time that microprocessor-based unit 110 generates a virtual reality trigger stimulus, a timer (e.g. clock circuit 154 of FIG. 4) is activated. If the patient or user does not activate the appropriate switch or control within a predetermined time interval, a digital signal is stored indicating a failure to respond. On the other hand, if the patient or user responds, a digital signal is stored indicating the user's reaction time (i.e. the time period between the occurrence of a virtual reality trigger stimulus and the patient's reaction).

Since a series of delayed reaction tasks is used in each audio or visual virtual reality delayed reaction test, the stored data that are accumulated during the virtual reality simulation will allow later analysis to determine various measures that relate to the patient's degree of attention. For example, measures that can be important include the patient's fastest reaction time, his or her mean reaction time, and the standard deviation of reaction times. In addition, the difference between the results for audio and visual delayed reaction tasks may also be considered. For example, young children tend to respond more quickly to audio trigger stimuli than video trigger stimuli. Thus, the relationship between the results of audio and video delayed reaction tests for a patient may provide some insight as to that patient's relative deficit or development of both auditory and visual attention skills.

Figure 5:
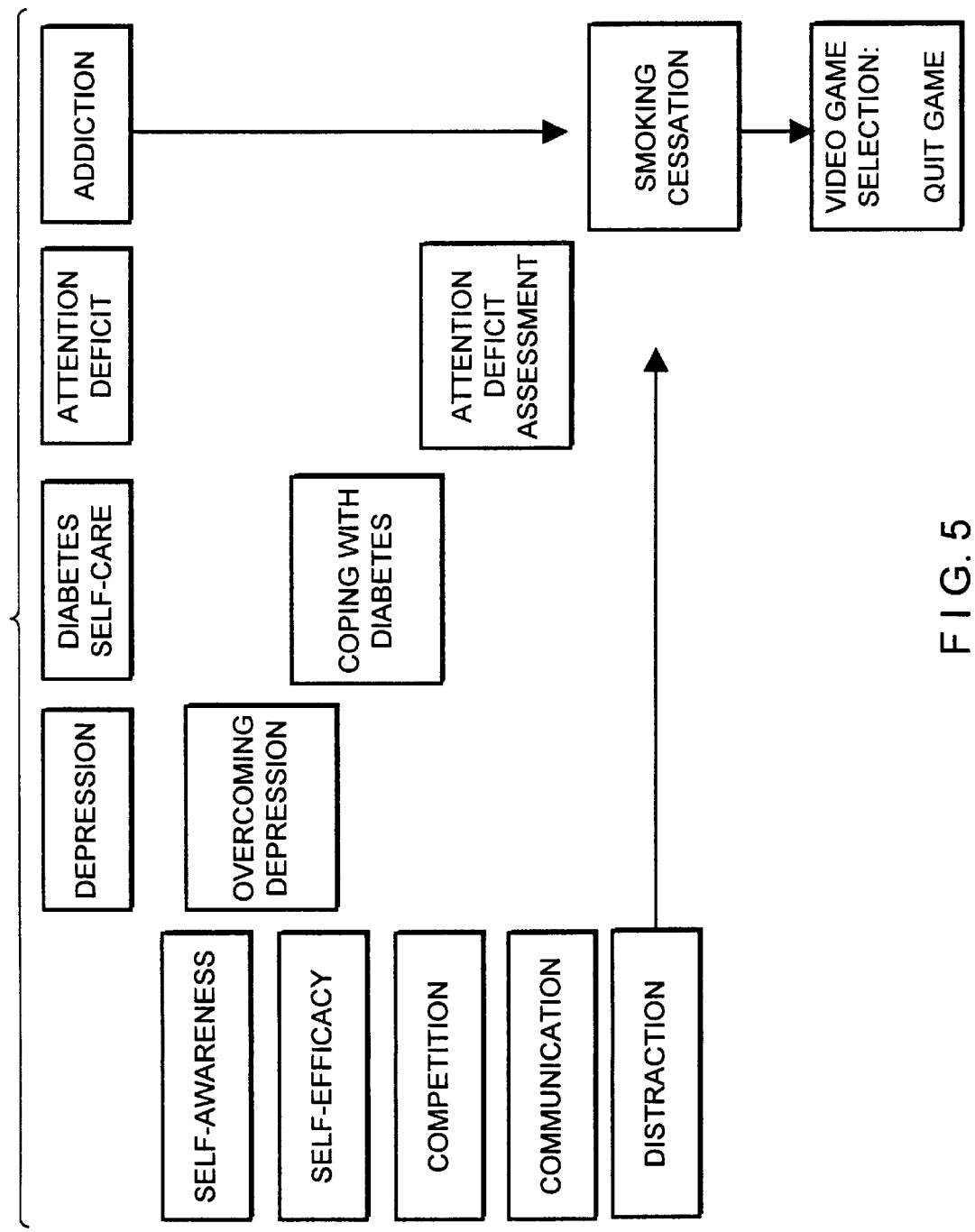
FIG. 5 is a flow chart illustrating how to select an appropriate virtual reality simulation treatment for some common medical conditions.

Although the above example describes a virtual reality simulation in the context of ADHD, this is only for illustrative purposes. Irrespective of whether or not the psychological condition/disorder is ADHD, as a general matter, before using microprocessor-based unit 10 shown in FIG. 1, a patient will first visit a physician or health care professional to evaluate his or her medical condition. The physician will diagnose the condition and choose the proper treatment based on patient needs. The flow chart in FIG. 5 shows the psychological strategies which the physician can select for treating depression, attention deficit, addiction and/or diabetes. The psychological strategies used in the virtual reality simulation may include self-awareness training, self efficacy training, competition, communication and distraction. Other strategies such as positive reinforcement, negative reinforcement, role-playing and the like can be employed as well. In addition to these, the psychological treatment strategy can include counseling methods and self-care instructions. Moreover, the treatment strategies can be combined as shown. For example, FIG. 5 shows overcoming depression is best accomplished by a therapy which joins self-awareness training with learning self-efficacy to regain control over one's life. In the particular case highlighted with two arrows, the medical condition to be treated is an addiction (such as smoking or alcoholism), and the appropriate psychological strategy for treating this condition is determined as distraction.

Once the psychological treatment strategy has been selected, the physician will choose an appropriate virtual reality simulation program comprising this strategy. Examples of virtual reality simulations based on the most common psychological strategies will be given in the specific examples to follow. The program is embodied within a computer-readable storage medium and/or transmitted using electromagnetic energy. The transmission of electromagnetic energy may be accomplished through the use of a carrier wave, and/or through the use of modulation techniques such as single-sideband (SSB) that suppress or eliminate the carrier wave from an electromagnetic signal. In the illustrative example of FIG. 1, the program is embodied in data storage medium 20 (FIG. 1). The virtual reality simulation program can be loaded from this medium 20 into microprocessor 12 and memory 18 of unit 10. This can be accomplished conveniently with a CD-ROM disk drive, since digital storage medium 20 is a CD disk.

The patient receives unit 10 prepared as described above and is instructed by the physician as to how and when to engage the virtual reality simulation. The physician may also load several virtual reality simulations at once and instruct the patient as to the appropriate time in which to engage each one. Depending on the type of virtual reality simulation and the patient's capabilities, the physician will also determine what patient input device 16 should be employed during the virtual reality simulation.

The patient takes home unit 10 prepared in this manner, and follows the prescribed treatment by engaging the virtual reality simulation. Once in operation, unit 10 displays a multidimensional virtual reality video simulation on display device 14 and receives input through patient input device 16. The beneficial effect of engaging the virtual reality simulation is available to the patient at any time in his/her own environment.

A particularly convenient method for delivering a virtual reality simulation to the patient is shown in FIG. 2. Handheld microprocessor unit 30 receives one or more virtual reality simulation programs from hospital computer 52. The virtual reality simulation program(s) are transmitted over a communications link implemented using any of various techniques for sending information from one location to another. In the example of FIG. 2, this communications link takes the form of a communication line 44 coupled to a remote communication unit 42 which receives information from the communication line 44. Unit 42 downloads the simulation programs into hand-held unit 30, for example, via connection cable 40.

Hand-held unit 30 in FIG. 2 also can communicate with clearing house 46 using a communications link such as, for example, communication line 44. As stated above, clearing house 46 can be a web server on the internet which is independent of the clinicians. The patient's progress throughout the virtual reality simulation can then be directly monitored by checking a set of simulation scores which are indicative of a patient's performance on the virtual reality simulation. This information is screened, classified, and sorted by clearing house 46. An abstract or report is transmitted through transmission line 48 to facsimile machine 50 which can be conveniently located in the physician's office.

Unit 30 shown in FIG. 2 can also be used by the patient to check her medical condition. To do this the patient follows instructions embedded in the virtual reality simulation which tells her to connect to unit 30, the measuring device 54 (e.g. blood glucose meter in the case of a patient with diabetes). Unit 30 and device 54 may also be hooked up permanently by the physician. The virtual reality simulation instructions tell the patient that to continue the simulation, she needs to perform a regular self-measurement using device 54.

For a patient with diabetes, this involves checking her blood glucose level by drawing a small blood sample into device 54. The measurement data are then downloaded into hand-held unit 30 to be used as input for the interactive video game session. An exemplary virtual reality simulation using this technique to collect data is described in Example 4, below. Meanwhile, the blood glucose-data is also passed through cable 40 to remote communication unit 42. From there the data follows the same path as described above for the simulation scores, and can be examined by the physician in the hospital.

The specific examples below describe exemplary microprocessor-based, interactive virtual reality simulation programs used for diagnosing and treating various medical conditions in human patients.

EXAMPLE 1

SMOKING

Figure 12A:
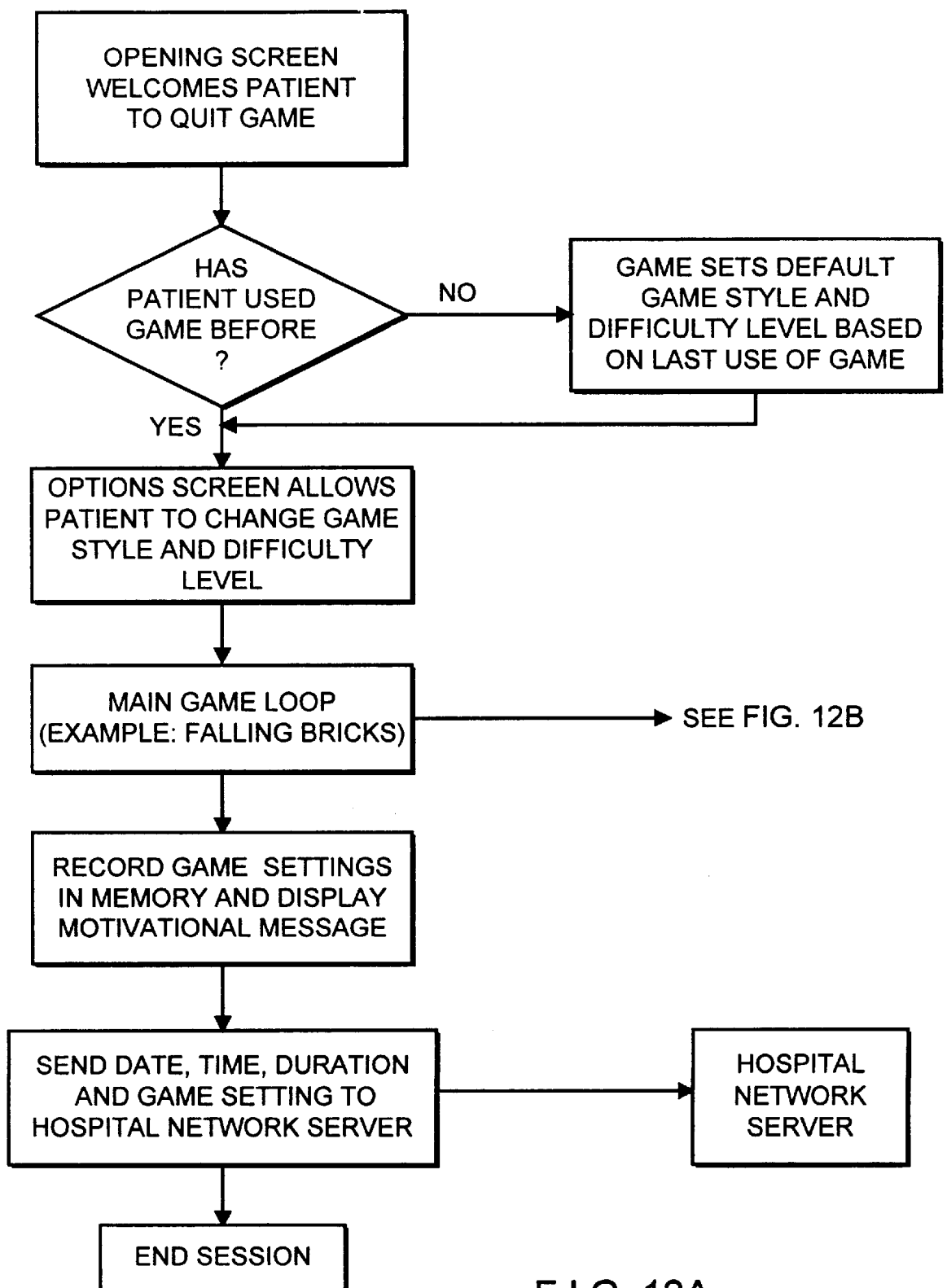
FIG. 12A is a general flowchart of an Addiction Distraction virtual reality simulation according to the present invention.
Figure 12B:
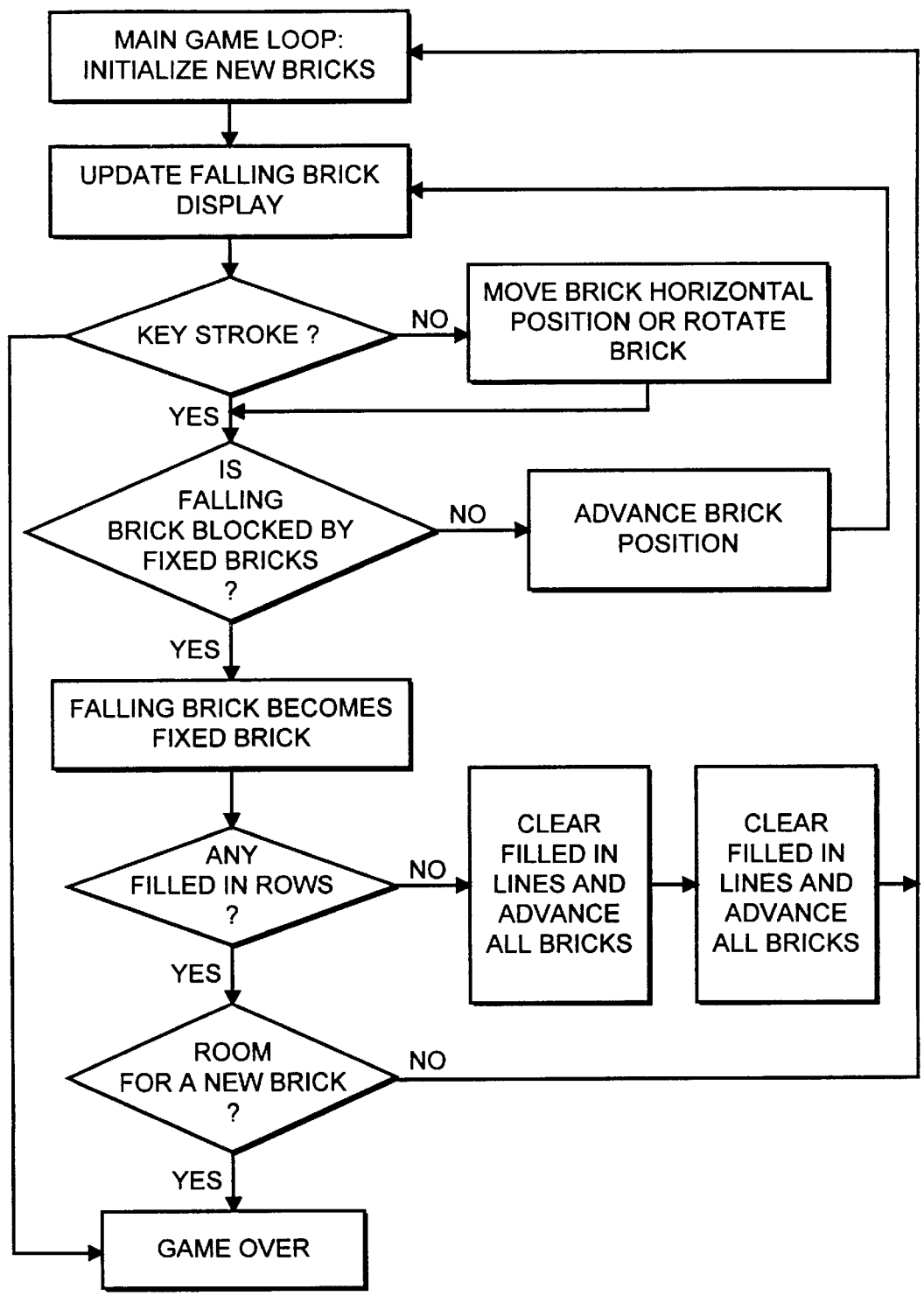
FIG. 12B is a detailed flowchart of the main game loop of the Addiction/Distraction virtual reality simulation shown in FIG. 12A.

The patient has a severe case of nicotine addiction. The physician determines, according to the flowchart in FIG. 5, that distraction is the best psychological strategy to induce the patient to quit smoking. (A strategy of punishment is not likely to prove effective). Therefore, the physician prescribes playing the "Quit Gamer", which is a virtual reality simulation containing a behavioral program based on distraction. This simulation contains graphical and/or three-dimensional characters engaging in various competitive activities upon proper input from the user. The smoker plays the game whenever he or she feels the urge to smoke. An exemplary virtual reality simulation to provide such an engaging distraction is shown in the flowchart of FIGS. 12A and 12B. In this example, the simulation is designed to distract the player with three-dimensional holographic projections of falling bricks which have to be stacked and arranged in rows.

During the simulation, the graphical and/or three-dimensional characters communicate to the patient instructions and simple strategies to quit smoking immediately, and advise the user—the patient—to take this approach, all within the context of an entertaining virtual reality simulation.

Alternatively, the simulation provides a timer and timeline for gradual reduction approaches to smoking cessation. Included among these programs are instructions for using nicotine patches. Built-in notification will serve to remind smokers to shift to a lower dose patch. Once the smoker has quit, the virtual reality simulation will provide a coping/relapse prevention model by using distraction methods during periods of smoking urges.

An analogous virtual reality simulation strategy may be followed in dealing with other substance abuse conditions, alcoholism, and obsessive-compulsive disorders.

EXAMPLE 2

GROWTH DISORDER

The physician diagnoses the patient with a growth disorder, such as Turner's Syndrome or a similar condition, requiring growth hormone treatment and a psychological treatment strategy for helping the patient to cope with his or her condition. By following a selection process similar to the one indicated in FIG. 5, the physician prescribes a virtual reality simulation combining self-awareness training, self-efficacy, role playing, counseling and competition.

In an illustrative virtual reality simulation program, a 3-dimensional graphical character, Packy, is a young elephant who, like the patient, is on growth hormone therapy. The simulation consists of three parts, each associated with a particular aspect of the treatment. In the first part, Packy encounters obstacles which he must surmount. In the second, Packy has to learn about growth hormone injections; and, in the third, he has to keep a personal growth diary.

Figure 6:
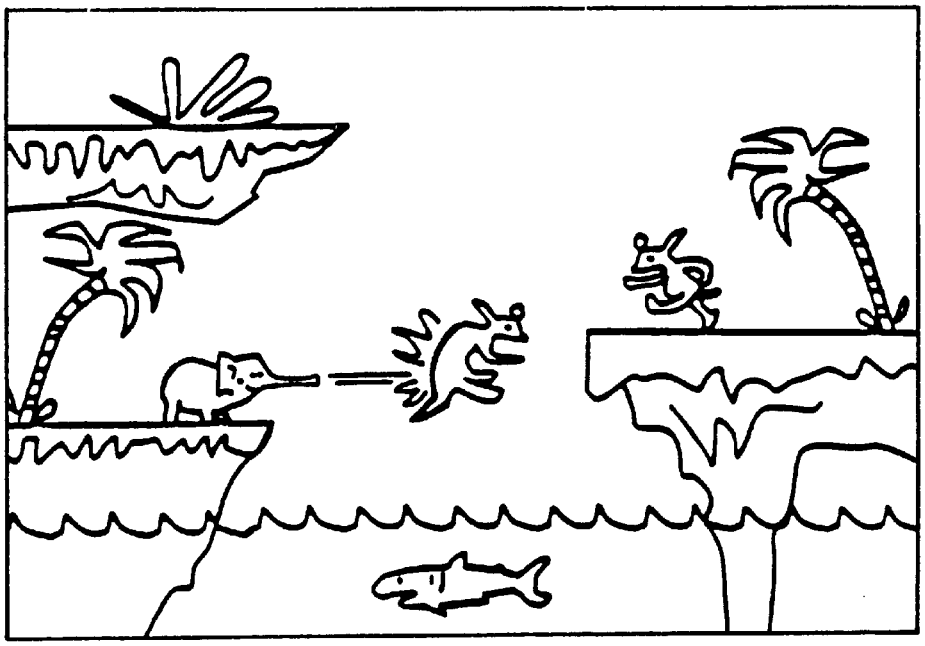
FIGS. 6 and 7 are exemplary screens of a virtual reality simulation for treating growth disorders.

In the first part, Packy learns about things that grow, from the smallest things in the world to the largest ones. In each level of this part, Packy can pick up three-dimensional icons of "OM" (representing a growth hormone shot) for a boost of energy. When he gets this boost, he will grow to a larger size until the energy wears out over time, until or he gets hit by one of his opponents in the form of 3-D villain characters. Every time Packy meets someone who challenges him, he must push them away by activating a virtual reality transducer to lower his head and walk into them, or he must squirt them by activating another virtual reality transducer. The small antagonists push and squirt away easily, but the large ones require some strategy such as combining pushing and squirting. This stage is depicted in FIG. 6. In each level, Packy will occasionally find obstacles that, in order to be overcome, require the patient to receive a growth shot. Packy will also occasionally encounter a guardian to the pathway that asks him questions from the information learned in the other two parts, i.e. the growth hormone injection instructions and the personal growth diary.

Figure 7:
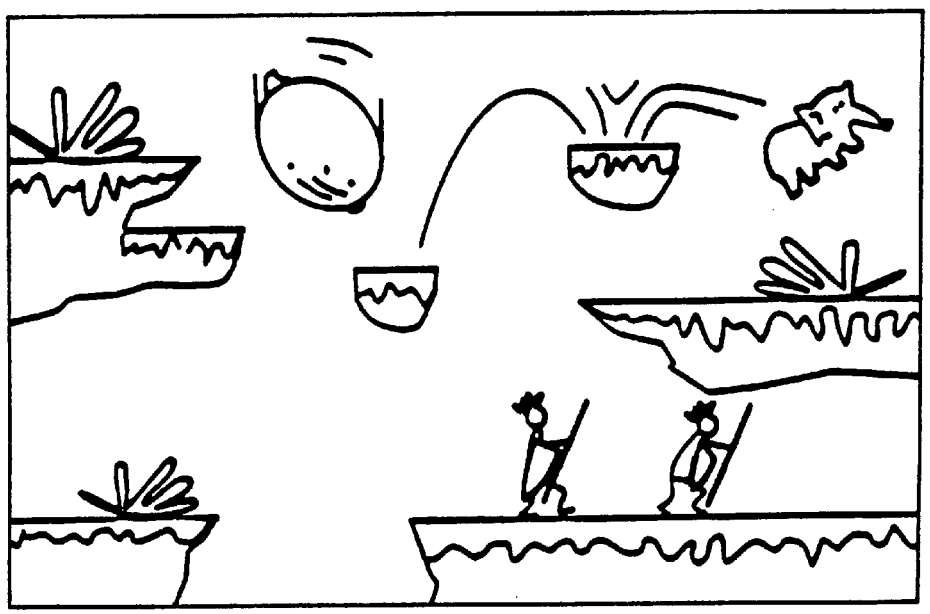

In another level of part one, Packy has a virtual reality, 3-dimensional dream in which he explores the world as a tiny creature. This scenario is illustrated in FIG. 7. He finds that he is very small himself, while all the surrounding items are very large. As he works his way to the end of this level, he will encounter all types of three-dimensional animals and insects that are very small. This level will give Packy a feeling for what it is like to be really small. In the transition to the next level, Packy will wake up and see that he is still the same size, and grateful that he is not so small.

In the final level, Packy finds himself very large. He will be with 3-D representations of various giant animals of the world. As he works his way through this level, he will encounter all types of animals that are very large, and the various types of obstacles that such large animals face in daily life. When Packy is bigger than the biggest elephant and cannot enter his home, he begins to realize the problems of being big.

Throughout his quest to feel comfortable with his growth, Packy is accompanied by a 3-D character in the form of a mosquito named Zippy. Zippy plays the role of a mentor and counsellor throughout the various levels of Packy's adventures. In part two, the patient will learn about preparing and administering doses of growth hormone. First, the user will see a virtual reality demonstration of how to mix a dose. Next, the user will be provided with virtual reality instructions on how to prepare an injection device, such as a needle and/or a syringe, for injecting the hormone. Finally, the user will be provided with a virtual reality demonstration showing how an injection is performed. This demonstration may be developed in a manner so as to alleviate any of the use's fears regarding injections. In the game aspect of this part, the user will be challenged to mix and administer a dose seven times (Monday through Sunday) and provide accurate results.

The third part of the virtual reality simulation is a growth diary where the patient records and sees various graphics displaying his or her personal progress. Playing this simulation is reassuring and helps children overcome growth disorders by emphasizing self awareness and self-efficacy training, role-playing, competition and counseling strategies embedded in the simulation. Analogous virtual reality simulation strategy is also used to treat anxiety and hyperactivity disorders, various types of phobias, as well as enuresis. The flowchart for the growth simulation is provided in FIG. 13.

EXAMPLE 3

DIABETES

Figure 9:
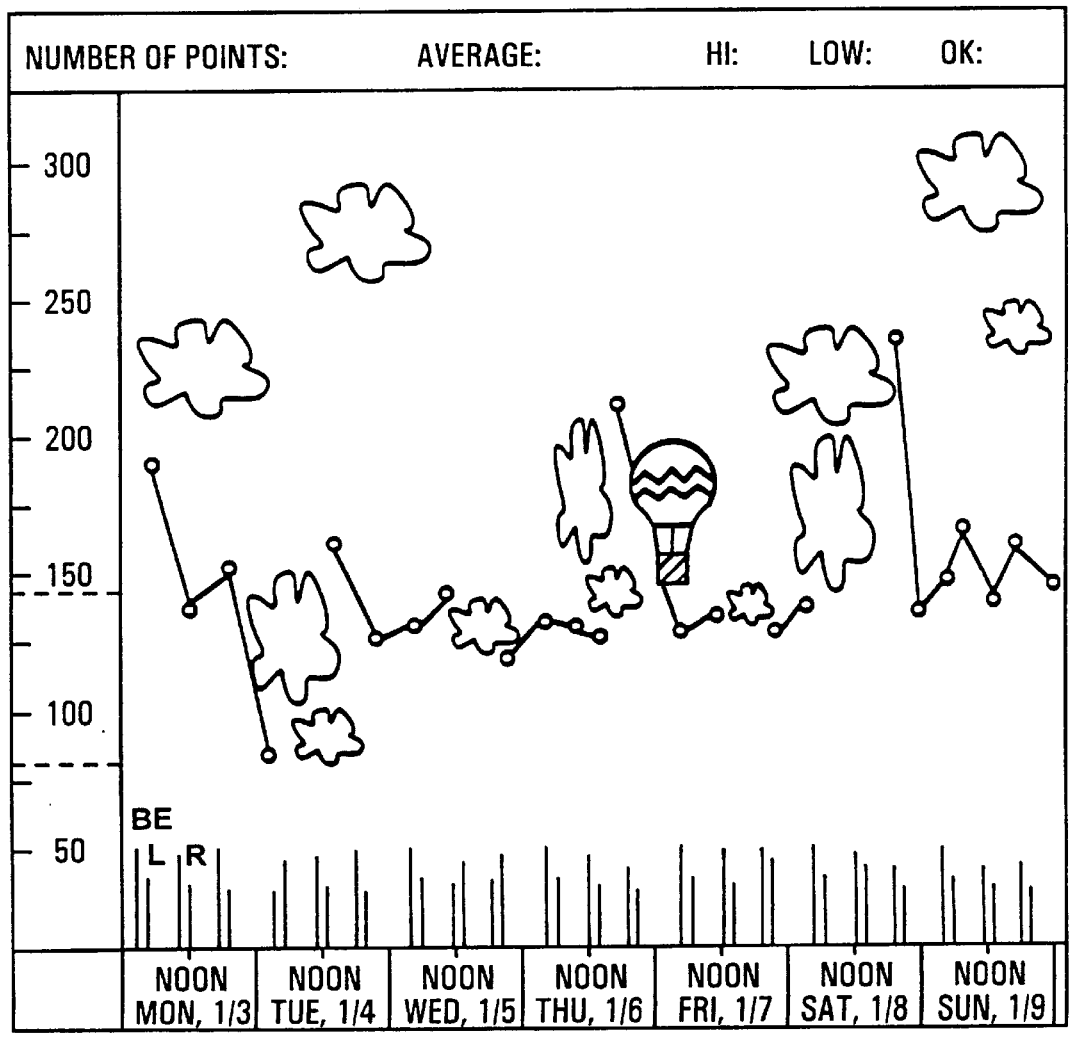

The patient is diagnosed with insulin-dependent diabetes. As treatment, the physician prescribes insulin shots and a virtual reality simulation based on positive-reinforcement and self-management. In the virtual reality simulation, the 3-D game character is a pilot who has diabetes, just like the patients. The pilot needs to follow a proper diet and exercise regimen in order to avoid crashing a plane or balloon which he is flying. Illustrative displays for the simulation are shown in FIG. 8 and FIG. 9. Eating wrong foods may cause blood glucose levels to increase, and the plane or balloon starts gaining altitude uncontrollably. Eventually, above a certain threshold, the balloon or plane spins out of control.

Figure 10:
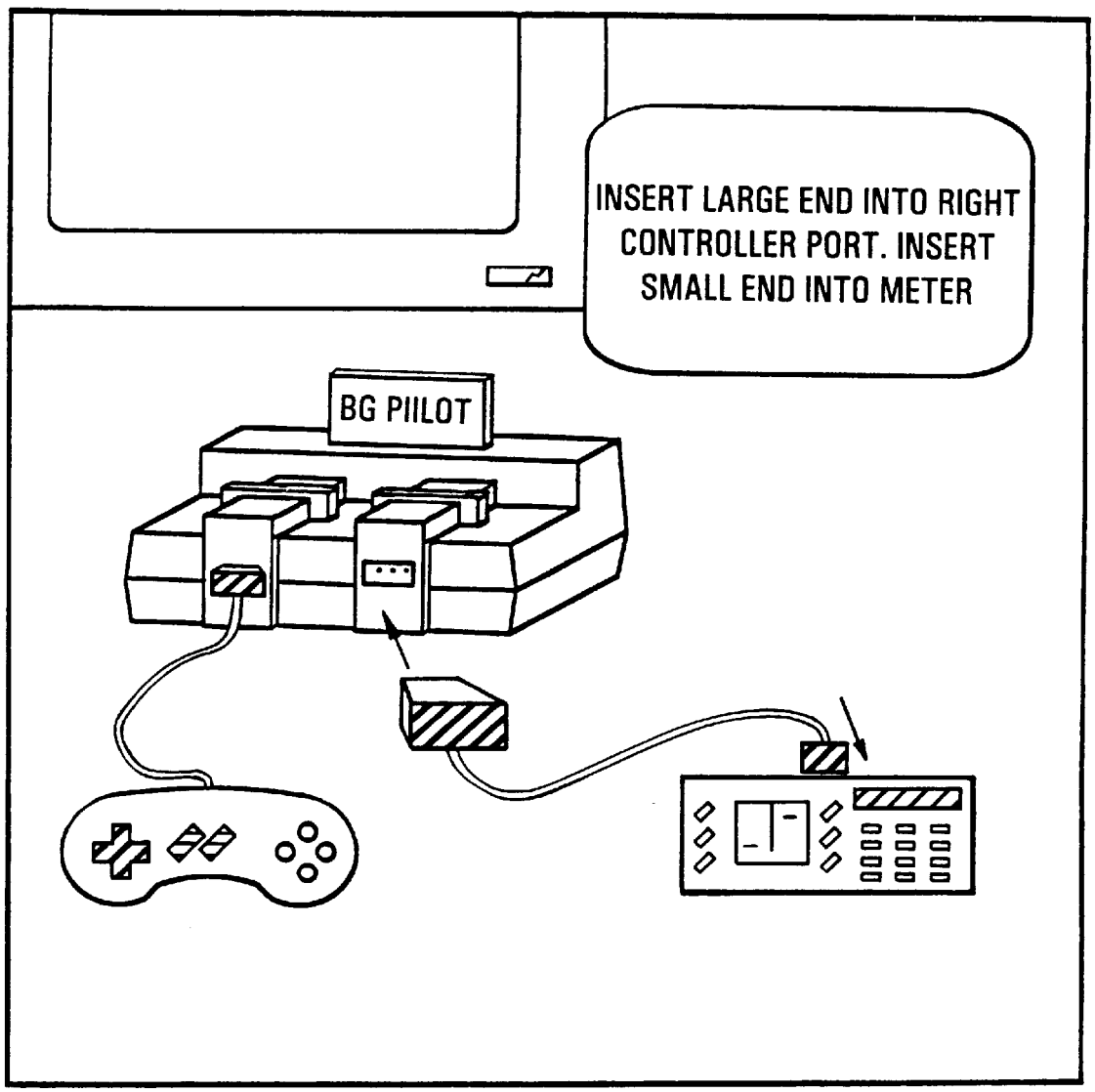
Figure 11:
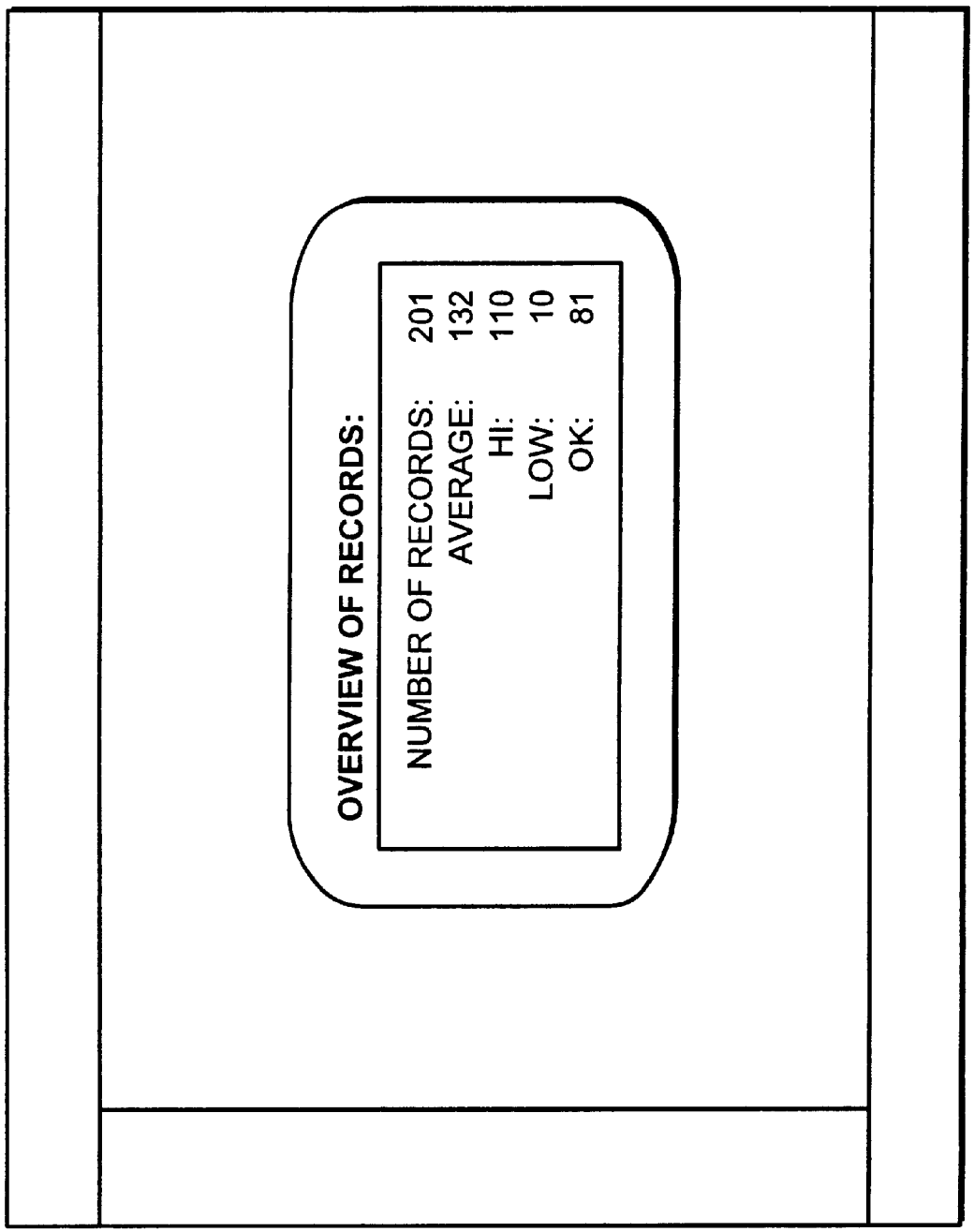
FIG. 11 is a screen indicating the blood glucose measurement results compiled for the virtual reality simulation of FIGS. 8–10.

During the simulation, the patient is requested to enter his own blood glucose level by using blood glucose meter 54. An exemplary set-up for doing this is shown in FIG. 10. The reading is used in the simulation and can also be transmitted to the hospital, as described in example 3. Also, the user can view his blood glucose readings in the form transmitted to the hospital and used in the simulation. An example of such reading for a number of measurement records is illustrated in FIG. 11.

If the user does not comply with the request for measuring and entering his blood glucose level, a three-dimensional representative of a plane or balloon disappears behind a representation of clouds, thereby signifying uncertainty in blood glucose levels. This is indicated by the clouds in FIGS. 8 and 9. The clouds obscure the pilot's vision and lead to collisions with objects in the plane's or balloon's path. Alternatively, if the blood glucose level drops below a minimum threshold, the plane or balloon crashes to the ground.

This positive reinforcement-based strategy, in which the blood glucose level is correlated to a virtual reality simulation parameter, e.g. plane altitude, teaches the patient how to cope with his condition on a day-to-day basis, while, at the same time making blood glucose monitoring fun. It also produces higher treatment compliance rates, especially in children who need to learn early on about proper diabetes self-management.

EXAMPLE 4

NONINSULIN DEPENDENT DIABETES MANAGEMENT

A virtual reality simulation treatment can be used for management of noninsulin dependent cases of diabetes (NIDDM). In such cases, the simulation is an interactive information resource, as well as a role-playing game. The simulation helps the patient, especially an adult patient, explore the topic of Staged Diabetes Management. The information could be presented in hypertext format, allowing the patient to select a stage, read a brief overview of it, and select details to examine it in greater depth. The simulation encourages active involvement in learning and provides opportunities to rehearse various health behaviors and see the consequences that result by observing what happens to a 3-D game character who displays these behaviors.

The contents of the simulation may be based on the Staged Diabetes management program, developed by the International Diabetes Center and Becton Dickinson & Company. The progressive set of stages ranges from least to most severe. For example, a patient in Stage I will learn to manage NIDDM through diet alone.

In the simulation, the user can configure the 3-D simulation character in many ways. A checklist of choices allows the patient to combine a variety of physical features and clothes, as well as specifics about the character's health status including weight, age, and medications taken. The character, and thus the patient, will make decisions in realistic settings such as restaurants and parties where rich foods are available. Also, an exercise plan will fit in with the character's busy schedule of family, community, and work commitments. This format provides the patient with a playful atmosphere in which choices which the patient faces in his or her own life can be rehearsed.

If blood glucose levels do not remain in the normal range in Stage I, the patient is instructed by the 3-D game character to advance to the next treatment steps, eventually arriving at the stage where the patient will be instructed to inject insulin to control blood glucose levels. The goal of the NIDDM game is to remain at Stage I.

Similar virtual reality simulations can help to deal with hemophilia, and other medical condition requiring the patient to be aware of his or her surroundings.

EXAMPLE 5

ASTHMA

A youngster diagnosed with asthma is given an asthma self-management virtual reality simulation for hand-held unit 30. The graphical simulated character, a young dinosaur from the pre-historic town of San Saurian, must cope with and manage his asthma. The simulated character confronts common asthma triggers, while learning to recognize early warning signs of an oncoming asthmatic episode. Asthma management techniques, including avoidance, relaxation, and medicinal inhalers, are part of the daily routine for the young dinosaur who must return to his cave. The dinosaur runs, jumps and shoots a squirt gun at oncoming triggers while conquering each level and mastering his condition. In addition to these inputs, the dinosaur requests the person engaged in the simulation to input his or her asthma condition by using physical parameter measuring device 54, which in this case is a respiratory flow meter. These data can then be transmitted to the physician as described above.

Playing a simulation which includes real asthma triggers, as well as relaxation techniques, affects the mental state of the player to improve his own asthma management outside of virtual reality sessions. This treatment based on role-playing and positive reinforcement makes the patient aware of the importance of prescribed drugs and teaches appropriate measures for dealing with the patients condition in real life situations.

EXAMPLE 6

EATING DISORDER

The physician determines that the patient suffers from an eating disorder causing the patient to gorge. The physician loads into the patient's microprocessor-based unit 10 or hand-held unit 30 a virtual reality simulation in which a graphical game character has to stay thin to survive. The challenges confronting the game character include avoiding fatty foods to stay trim, while, at the same time, eating a sufficient amount of healthy foods to combat dragons and surmount obstacles. Doing this involves making choices about what food presented on the screen to eat, keep for later, or reject. Wrong food choices have diet consequences in the graphical character's ability to survive. The simulation is scored according to the length of time the patient keep the game character alive, and the number of obstacles the character overcomes.

The physician instructs the patient to play the simulation every time the patient feels an eating urge outside regular meal times. During a regular follow-up visit, the doctor evaluates the patient's progress and checks the scores obtained in playing the simulation. Based on the analysis of the scores, the physician determines the severity of the problem and obtains an insight into the patient's motivation to comply with the therapy.

Sufficiently high scores reflect progress and readiness to proceed with the next treatment stage. At this point, the physician may instruct the patient to play another simulation designed for milder eating disorders, or a simulation utilizing a different psychological approach, e.g. negative reinforcement or distraction.

EXAMPLE 7

DEPRESSION

A psychiatrist enrolls a patient in a series of home-based interactive virtual reality simulation sessions which the patient accesses from his microprocessor-based unit 10 through hospital network 26. The simulation is then transmitted from the hospital network server 28 to the patient in unit 10. The simulation involves interaction with a graphical game character resembling the Yoda character from the popular movie "Star Wars". Yoda acts as a counselor and mentor to the patient, preparing him for various trial episodes in the simulation. Based on the patient's scores in playing the simulation, the physician reviews how the patient responds to this type of treatment, and prepares another simulation to be transmitted to the patient. This treatment method is part of an on-going therapy for mild to medium-severe depression. This approach may also be used for schizophrenia and other psychological disorders.

EXAMPLE 8

ATTENTION DEFICIT HYPERACTIVITY DISORDER

A home-based, highly motivating virtual reality simulation that includes continuous performance tasks can serve two important management functions for children with ADHD, both of which are currently unavailable. First, it gives these children opportunities to practice tasks requiring sustained attention and receive performance feedback within an educational simulation designed to improve their knowledge and attitudes about ADHD. Second, it provides a home- or school-based continuous performance task that would have great value as an additional, objective outcome measure in double-blind trials of medication for ADHD.

Following the virtual reality simulation, an interactive multimedia intervention protocol for ADHD may be performed. Such intervention may include two components—(1) a virtual reality simulation that offers experiential education about focusing attention and controlling impulsiveness, and (2) a multimodal assessment for medication management.

The experiential education simulation provides, in an action oriented simulation, opportunities to practice focus of attention and control of impulses, supportive and educational performance feedback and general information about ADHD and its treatment. The medication management system will allow patients to use a virtual reality simulation battery of continuous performance tasks and then send the results via a communications link (i.e., any of various ways of communicating information from one location to another, including wireless as well as wired technology) from home to a central computer that will enable communication of data directly from the child's home to the physician. Parents and teachers will respond to behavior rating scales via the communications link so that multimodal assessment can be accomplished conveniently and at low cost on a daily basis.

The situation-dependent nature of ADHD indicates the need for a comprehensive test, as an attention deficiency is not always apparent in a clinical environment. The ADHD intervention allows for a multilateral approach. Data will be collected from parents and teachers through the use of questionnaires they can answer suing the virtual reality simulation.

Data from the children will include their test results in the simulation, in the form of a battery of Continuous Performance Tasks (CPT battery). The simulation coordinating this approach will include a data collection system (electronic questionnaires and CPT battery results), a modem that will send the data from the virtual reality simulation to a central EBM computer via telephone lines, and a data analysis system with statistical tools that can generate clinical reports about individual patients and can aggregate data about many ADHD patients for use in epidemiological research.

The medication management system which can comprise an intervention simulation, a communications link establishment device and an IBM™ and/or Mac™ compatible reporting system will be available to health care providers and researchers.

Studies of adults reveal that adults learn more efficiently with well-designed multimedia than with print, video, or traditional classroom teaching; generally enjoy learning with multimedia more than with other materials and methods; and increase their motivation to learn about the topic when they use multimedia that meets their instructional and informational needs. These findings are identical to those in studies with younger people. The ADHD intervention according to the present invention and as outlined below, will appeal to a wide audience of adolescents and adults, even though the virtual reality simulation might be targeted to ages 6 to 12.

In one illustrative virtual reality simulation, the child watches the screen as a car drives past mountain scenery and a line of trees. This simulation is designed to assess the test subject's visual continuous performance ability. Each tree bears one or more fruits, such as mangoes, grapes, apples, oranges, passion fruit, and/or lemons, one of which is the target fruit and is designated as the signal. The child is instructed to press a response button each time the car passes the target fruit. When the button is pressed, a net reaches up from the car to grab the fruit with appropriate sound effects. If the fruit is a correct target fruit, the car speeds up, as evidenced by a shorter interstimulus interval (ISI) between trees and an increase in the pitch of the car engine sound. Missing the target fruit, or impulsively pressing on a non-target fruit, will slow the ISI and lower the engine sound, thereby slowing the car. If the child presses the button after the fruit has passed the car, but while it is still on the screen, it is defined as a late hit and the ISI and engine speed are not adjusted. In this way, a miss due to reaction time alone will not be recorded as a miss and the speed will remain constant. During the distraction phase of the visual continuous performance task, butterflies, birds, flying saucers, and frogs are also moving on the screen to distract the child from the target stimuli.

In an illustrative virtual reality simulation to test for auditory continuous performance, the car is driving past the trees at night with headlights that illuminate the tree trunks, but incompletely illuminate the fruit in the trees. The child must listen for either a high pitched beep (indicating a target) or a low pitched beep (indicating a non-target) and respond accordingly. The speed of the trees and the auditory clues from the net and the engine speed continue to reinforce the child on correct hits. During the distraction phase of the auditory continuous performance task, a digitized voice of a child randomly says "Press it," "Now," and "Go" to distract the child from the correct beeps.

The result of each simulation is sent to the administrator program, which calculates the minimum, mean, standard deviation and number of false starts. Each phase of the simulation (visual or auditory, undistracted or distracted) is calculated separately. Thirty-two evenly spaced samples of the ISI may be taken during each phase. These are then averaged for each test, or they can be displayed graphically. The administrator program also records the number of targets missed, the number of impulsive hits, and the number of late hits.

ADHD Intervention

The ADHD intervention has two components—(1) an educational virtual reality simulation and (2) a medication management system. The following is a description of the simulation and the medication management system.

The ADHD virtual reality simulation delivers experiential education by providing opportunities for children to practice their attention skills. It is targeted in terms of themes, characters, reading level, and difficulty of game play-to children ages 6 to 12. Children who play the simulation will engage in continuous performance tasks (CPT's), rehearse attention skills during game play and learn about ADHD, all in the framework of a simulation game.

In the ADHD simulation, children play the role of a rabbit, or two rabbits in two-player mode, all of whom have ADHD. They will be challenged to reach a destination quickly. For example, they may have to save someone before time runs out. Or, they may have to go somewhere, find something of value, and bring it back fast. These types of scenarios can be used in a simulation strategy that requires speed and accuracy, skills that ADHD children typically need to practice because attentional focus and concentration are required. The simulation alternates between (1) CPT'S, where the rabbit is in a vehicle, and (2) side-scrolling, action simulations where the rabbit is on foot and still trying to reach the destination. The CPT's involve a vehicle-car, boat, and then space ship-the same way the prototype used a car racing along a road while the player was asked to press a button to grab targets.

When the simulation starts up, it gives the player two options—(1) Races or (2) Game. The races are the CPT's and DRT'S. The player goes through six in a row and receives a score on each one. The faces are used for fan or can be assigned under the supervision of a clinician for assessment, or during double-blind medication trials. The tasks are:

1. Visual Delayed Reaction Time Task
2. Auditory Delayed Reaction Time Task
3. Visual Continuous Performance Task
4. Visual Continuous Performance Task with visual distractions
5. Auditory Continuous Performance Task
6. Auditory Continuous Performance Task with auditory distractions The simulation will continue until 12 CPT's and 12 game levels are completed, and the simulation levels will increase in difficulty. This will allow the six CPT's each to be repeated twice. It will also make the simulation long and challenging enough to maintain the childrens' interest for many sessions. To this end, it is typical for children to spend 40 to 60 hours, over several months, playing a challenging NINTENDO™ game until they can complete every level. In the present example, each level of the simulation will require skills that were rehearsed in a previous CPT or DRT. Players will receive individualized feedback about their skill in the simulation on these tasks. Feedback will refer to their previous performance in the CPT or DRT. Players will receive bonus points for successfully accomplishing the CPT and DRT tasks within the simulation levels.

Throughout the simulation levels, players must look for an icon, for example a red rose, which provides information about ADHD. The information deals with symptoms, medication, behavior management, environmental accommodations, social skills, and family and peer relationships. When more than one child plays the simulation, each controlling the actions of a rabbit, they will soon realize that it is advantageous to cooperate. The rabbits will gain the most points if they wait their turn, stay close together (which requires at least one child to pay attention to the location of their partner's rabbit), and give each other what they need (supplies, food, jewels etc.), so both of them can have peak strength and power to meet oncoming challenges.

The virtual reality simulation will improve the self-concepts and self-esteem of children with ADHD; improve attitudes about ADHD, and increase their motivation to learn more about it; enhance children's willingness to talk about ADHD with friends, family and clinicians; increase children's knowledge about ADHD; teach children some of the skills needed to focus attention and control impulses; and contribute to a decrease in behavioral problems at home and at school.

Medication Management System

The ADHD intervention provides the option to play the races virtual reality simulation only. The Races are CPT's and DRT's presented in an appealing and motivating format that children enjoy. Double-blind medication trials can occur daily, at home, with data transmitted via modem to a central computer. Patients send their daily data via a telephone link, and the central computer collects, analyzes and reports the data. Parents complete on-line rating scales, and teachers fill out paper versions of rating scales. These data are compiled, and a report sent to physicians as soon as the patient's double-blind trials are completed.

The medication management system supports a multilateral approach to medication management. The system provides a convenient way for parents to respond to rating scales and for patients to take a computer-based assessment battery with results sent electronically to clinicians. The system reduces the time and clinical costs involved in double-blind trials, and provides a method for administering double-blind trials and a powerful tool for epidemiological researchers to analyze aggregate data collected from ADHD patients.

Stimulant medication has been repeatedly demonstrated to have a beneficial short-term effect on the core symptoms of ADHD. However, choosing the proper dose and differentiating real therapeutic effects from expectation and placebo effects is not easily done with known methods. The virtual reality simulations, in conjunction with medicinal therapy, as presented by this invention, enable a determination of the most appropriate dose, and monitor for side effects at different doses.

The medication monitoring mode of the ADHD intervention is designed to assist in the daily home measurement of medication effects, including a behavioral rating scale, a side effects scale, and a continuous performance test, and to transmit this to the clinician on a daily basis for analysis.

Figure 14:
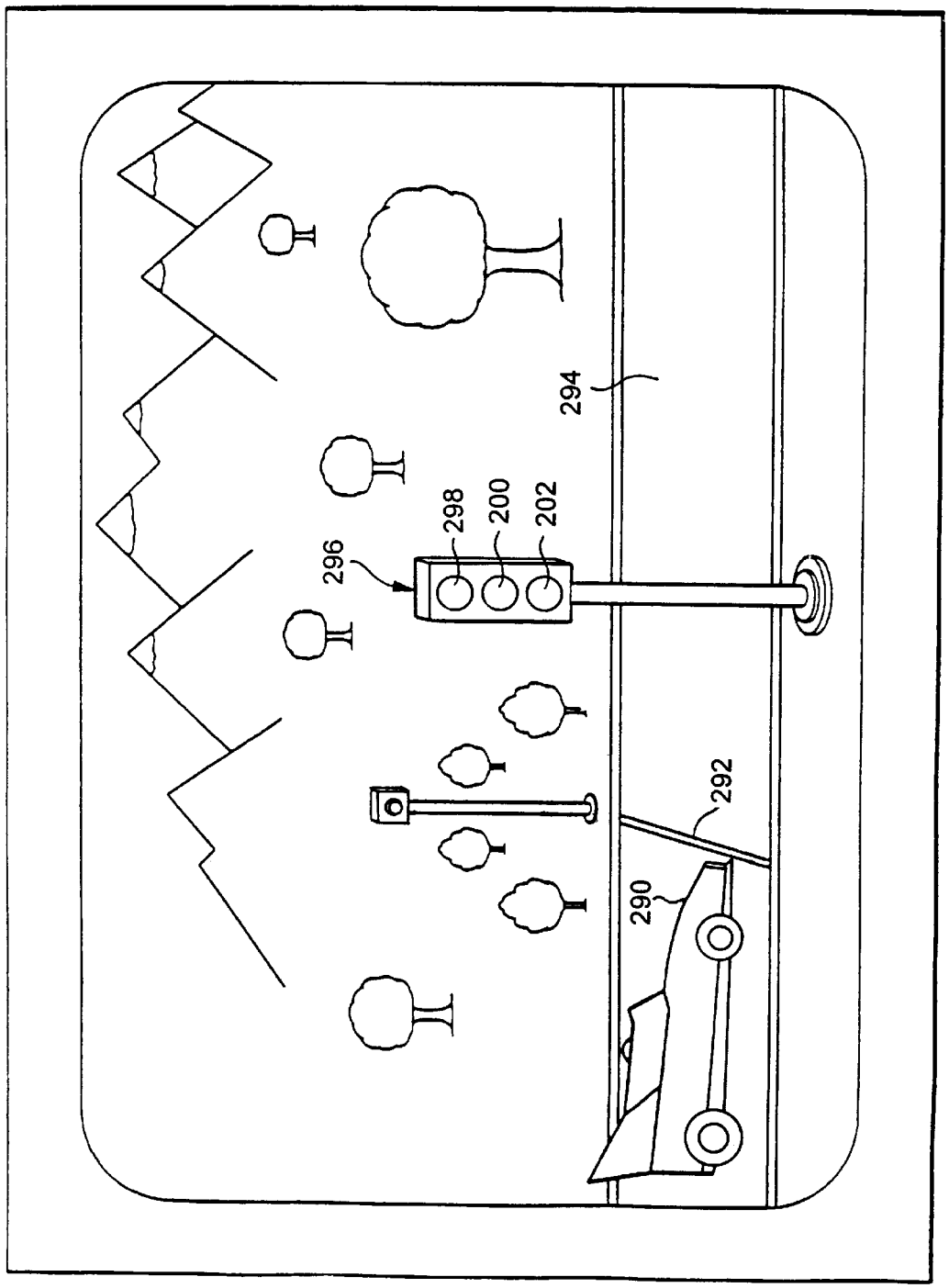
FIG. 14 illustrates a multidimensional graphic display suitable for use when a microprocessor-based patient unit administers a delayed reaction test in an embodiment of the invention that is configured for diagnostic measurements relating to Attention Deficit Hyperactivity Disorder (ADHD).

FIG. 14 shows an exemplary 2-dimensional projection of a 3-dimensional image field projected by the screen display. This projection represents an ADHD virtual reality simulation display. A car 290 is positioned at a starting line 292 on a roadway or racetrack 294. A traffic signal 296, having a red light 298, an amber light 200, and a green light 202, is prominently displayed. As each visual delayed reaction task is generated, microprocessor-based unit 110 (FIG. 3) causes sequential illumination of red light 198, amber light 200, and green light 202. Amber light 200 serves as the warning stimulus, with green light 202 providing a trigger stimulus after a randomly generated time delay that is within the time delay range that was established when the visual delayed reaction test being executed was established by the clinician or the administrator having control over the diagnostic testing.

During the audio delayed reaction tests, the three lights of traffic light 200 in FIG. 14 are extinguished and program instructions that are stored in external memory unit 112 (FIG. 3) result in generation of suitable audio warning and trigger stimuli by sound generator 162 of FIG. 4.

In arrangements having sufficient memory and sound generation capability, the words "ready . . . set . . . go" are used with the time interval between "set" and "go" being a random value within A range of values selected when a clinician established the diagnostic procedure. Two tones that are clearly distinct from one another also can be used for the warning and trigger stimuli. In some virtual reality simulations, both visual and audible continuous performance tests can be administered. In each test, a sequence or series of events occurs for which the patient or user is to respond by activating a predetermined switch or control such as the control switches 144 in the arrangement of FIG. 4.

Any continuous performance tests that are used in a given virtual reality simluation can, but need not, be performance-paced. Performance-pacing refers to the notion that the inter-stimulus interval (i.e. the time that elapses between consecutive stimuli) is reduced by a predetermined amount each time a correct response is made. Likewise, the inter-stimulus interval is increased by the same or a different predetermined amount if an improper response occurs (i.e. the user responds to a non-target stimulus or fails to respond to a target stimulus).

Figure 15:
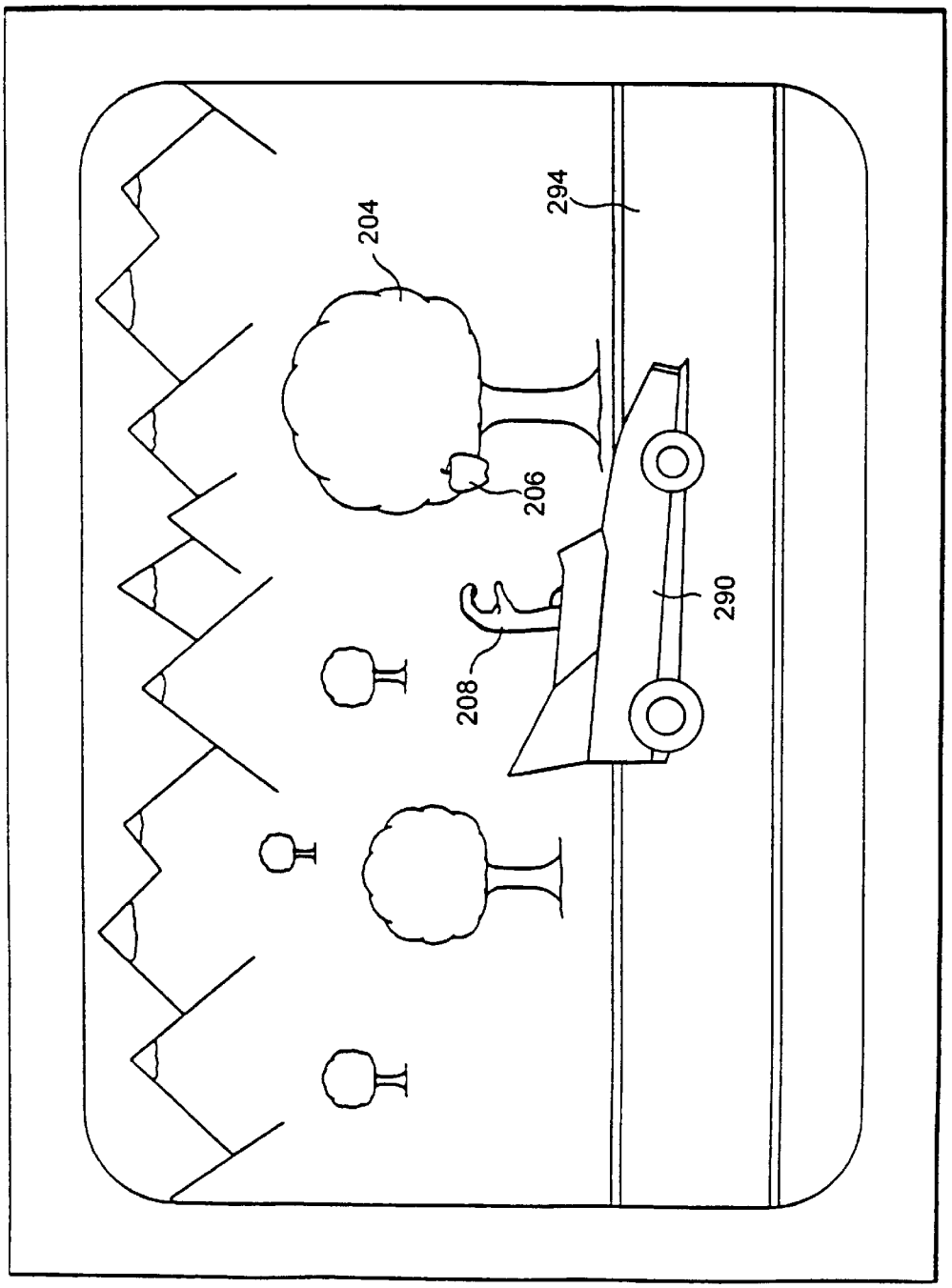
FIG. 15 illustrates a graphic display suitable for use when a microprocessor-based patient unit administers continuous performance tests for diagnostic measurement relating to ADHD.

A two-dimensional projection of a 3-dimensional image field for an illustrative virtual reality simulation is shown in FIG. 15. This simulation implements continuous performance tests. In FIG. 15, the car 290 that is used in the above-discussed delayed reaction tests is shown traveling along a roadway 294. Periodically, the car 290 approaches a tree 204, which is positioned along side roadway 294. As car 290 approaches a tree 204, various types of fruit (oranges, apples, lemons and grapes) will appear, hanging downwardly from a branch of the tree. The object is for the patient or user to respond to a specified type of fruit only (e.g. apple 206 in FIG. 15) by depressing a selected switch such as one of the switches of control switches 144 in FIG. 4. When the appropriate switch is pressed, a hand and arm extend upwardly from car 290 to capture the fruit. As previously noted, with each correct response, the interstimulus interval is decreased (i.e. car 290 appears to travel at a higher rate of speed) and with each incorrect response or failure to respond, the interstimulus interval is increased (car 290 appears to travel slower).

In the audio continuous performance tests of the referenced realizations of the invention, the display shows an image field including a car 290 traveling at night, with only a portion of roadway 294 being illuminated by the car's headlights. Each time the car approaches a darkened tree 204, a low-frequency radar-like "beep" is heard if the tree does not bear is present, the desired fruit (apple 206, FIG. 15). When the proper fruit a high-pitched radar-like beep is emitted.

Figure 16:
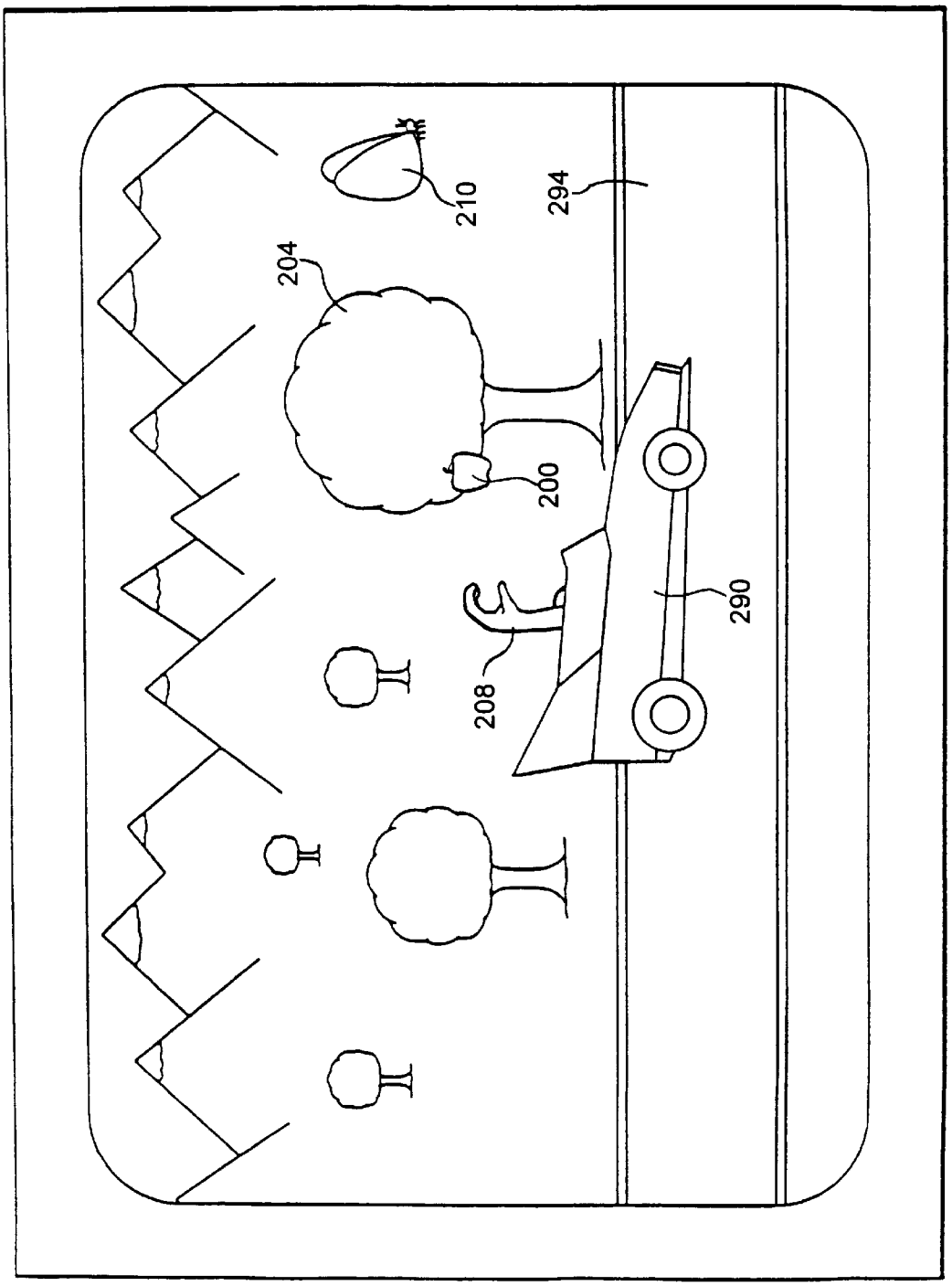
FIG. 16 illustrates a graphic display suitable for use when a microprocessor-based patient unit administers continuous performance tests that also include visual distractions for diagnostic measurements for ADHD.
Figure 17:
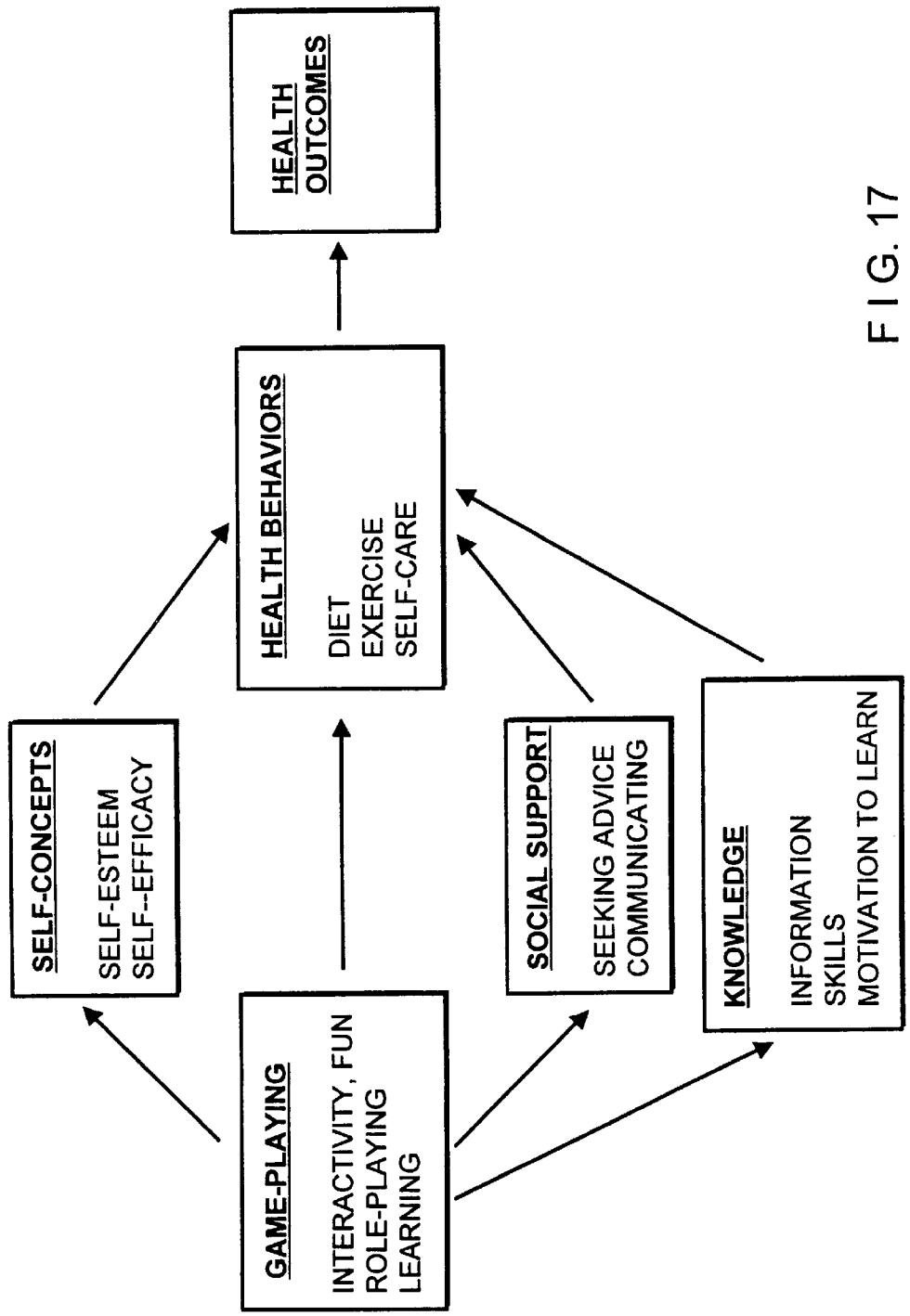
FIG. 17 is a detailed flowchart for the ADHD virtual reality simulation according to the present invention.

Embodiments of the invention for diagnostic assessment for ADHD can also include programming for conduction of continuous performance tests that include distractions. For example, as is shown in FIG. 16, a 3-D projection of a fluttering butterfly 210 or other moving object, such as a hopping frog or flying saucer, can be generated in the peripheral region of the video display to provide a measure of the patient's degree of distractibility. During audio continuous performance tests, synthesized voice signals such as "Now!" or "Go!" can be generated by the microprocessor-based unit 110 (FIG. 3). In situations in which synthesized voice is beyond the capability of the sound generator being used, the microprocessor-based unit 110 can supply various distractive sounds or noises. When the battery of diagnostic assessments is established by a clinician, simulation instructions can be stored in external memory unit 112 (FIG. 3) or otherwise provided to a microprocessor-based unit, to determine the number of continuous performance tests to be performed and the type of each test (i.e. video without distractions; video with distractions; audio without distractions; and audio with distractions). The sequence of the tests, both with respect to one another and with respect to the previously discussed delayed reaction tests, is also determined by the clinician. For each continuous performance test, the clinician can select the total number of target and non-target stimuli to be presented; the test duration; and the minimum stimulus duration (which is typically set at around 100 milliseconds). Diagnostic measures that are recorded in external memory unit 112 during conduction of continuous performance tests include: the number of target stimuli correctly identified (i.e. captured); the number of target stimuli for which the user failed to react (missed stimuli); the number of non-target stimuli for which there was a response; the number of times the button or switch was activated after a stimulus passed (late hits); and the final interstimulus interval (and/or the minimum interstimulus interval attained during the test).

As was described relative to FIGS. 3 and 4, simulation instructions for establishing the diagnostic assessment procedure (e.g. storing suitable program instructions in external memory 112) and retrieval of signals representative of the diagnostic measures gathered during diagnostic testing (e.g. accessing information stored in external memory 112) are performed by executing an administrator program with the clinician's computer (122 in FIG. 3; digital signal processing unit 142 in FIG. 4). When the administrator program of the current realizations of the intention is executed, a main menu screen is displayed, allowing the clinician to select menu items that include: the opening of a new file (i.e. establishing a diagnostic assessment procedure for a new patient or subject); opening an existing file; saving a file (storing a diagnostic assessment configuration in memory of the clinician's computer); closing a file; and producing the diagnostic assessment procedure (i.e. storing the appropriate simulation instructions in an external memory 112 or, alternatively, initiating execution of a diagnostic assessment procedure with a microprocessor-based unit 110 that is directly connected to the clinician's computer (FIG. 4).

Presented herein is a method for treating medical conditions in human patients using a microprocessor-based virtual reality simulation. This method gives a better picture of the ailment through its standardized scoring procedure and makes the treatment much less costly by considerably reducing the number of therapy sessions with the physician or health care professional. In addition, virtual reality simulations provide the opportunity of treatment in the patient's own environment. This leads to self-help responses difficult to foster in therapy sessions. The patient recognizes the importance of medications and treatment regimens in an entertaining manner. Moreover, the patient participates actively in the treatment by following instructions embedded in the virtual reality simulation or even generating positive physiological responses due to stimuli presented in the video game.

The method of the invention also provides a treatment to which the patient can resort as the need arises. The intrinsic fun in playing virtual reality simulations ensures higher treatment compliance for all patients, and in particular children. The self-treatment instructions communicated by this method can be used to additionally induce patients to independently perform measurements of physical parameters associated with their medical condition.

Finally, the scoring of the simulation provides an excellent standardized measure for evaluating treatment results and improving continued treatment. In carrying out this method, the microprocessor-based system can be expanded to use any number of communications devices, monitoring set-ups, and other state-of-the-art medical equipment. Therefore, the scope of the invention should be determined, not by examples given, but by the appended claims and their substantial equivalents.

Various modifications and alterations to the present invention may be appreciated based on a review of this disclosure. These changes and additions are intended to be within the scope and spirit of this invention as defined by the following claims.

What is claimed is:

1. A microprocessor-controlled virtual reality simulation apparatus adapted to diagnose a psychological condition and/or disorder presented by a user, the apparatus adapted to generate visual displays representing three or more dimensions as a first series of outputs provided to a display device, the first series of outputs directed to aid in diagnosis of the psychological condition and/or disorder, the simulation apparatus comprising:

a controlling mechanism for controlling the simulation apparatus using one or more stored protocols, wherein each protocol is related to diagnosis of a specified psychological condition and/or disorder, and the protocol is comprised of display controlling functions for controlling one or more three-dimensional graphical elements presented on the display;

an input mechanism adapted to accept any of a plurality of user-generated inputs interactively entered by the user in response to the first series of outputs; and an output mechanism for relaying a second series of outputs to a health care professional, wherein the second series of outputs are specifically configured to provide a presentation of one or more user-generated inputs to the health care professional for diagnosing the psychological disorder and/or condition.

2. The apparatus of claim 1 wherein the protocol includes programming commands for manipulating at least one three-dimensional graphical character presented on the display.

3. The apparatus of claim 1 further comprising:

a linking device for linking the apparatus to a network, the linking device comprising an interface device for interfacing the microprocessor to the network; and at least one peripheral server linked to the network, the server to receive the inputs and the outputs, and adapted to exchange data within the network.

4. The apparatus of claim 3, wherein the server comprises: a receiver for receiving the inputs and the outputs; a memory device for storing the inputs and the outputs; and a processing mechanism for processing the inputs and the outputs, further including a second microprocessor-controlled data processing unit in communication with the apparatus, wherein the second microprocessor controlled data processing unit is adapted to process and exchange data with the apparatus.

5. The apparatus of claim 1, wherein the psychological disorder and/or condition for diagnosis is selected from the group consisting of ADHD, schizophrenia, depression, hyperactivity, phobias, panic attacks, anxiety, overeating, compulsive behaviors, addictions and substance abuse.

6. The apparatus of claim 1, wherein the stored protocol is specifically configured to provide a test battery of continuous performance tasks to the user through the display, and wherein the apparatus further comprises a data collection subsystem for storing and analyzing the user's inputs responsive to the battery and relaying the analytic results via the second series of outputs to the health care professional for diagnosing the psychological disorder and/or condition.

7. The apparatus of claim 6, wherein the psychological disorder for diagnosis is ADHD, the battery further comprises auditory and visual delayed reaction time tests for attention, and wherein the subsystem comprises an administrator program for configuring the tests.

8. In a system equipped to access instructions for an interactive virtual reality simulation configured for a specified psychological disorder and also adapted to receive input data from the patient, wherein the system includes a multi-dimensional display adapted to provide three-dimensional image projections to the patient, the system further comprising a stored protocol directed to diagnosis criteria for the psychological disorder, a method for diagnosing a psychological disorder in a patient comprising the steps of:

a) loading the instructions into the system;

b) instructing the human patient on how to use the system to play the interactive virtual reality simulation; and c) collecting the input data from the patient and analyzing the data to arrive at a diagnosis.

9. The method of claim 8, wherein the psychological disorder for diagnosis is selected from the group consisting of Attention Deficit Hyperactivity Disorder (ADHD), one or more ADHD subcategories, schizophrenia, depression, hyperactivity, phobias, panic attacks, anxiety, overeating, compulsive behaviors, addictions and substance abuse.

10. The method of claim 8, wherein the stored protocol is specifically configured to provide a test battery of continuous performance tasks to the patient through the multidimensional display, and wherein the input data from the patient responsive to the test battery is analyzed for diagnosing the psychological disorder.

11. The method of claim 10, wherein the battery further comprises auditory and visual delayed reaction time tests for attention.

12. The method of claim 10, wherein the protocol analyzes the input data from the patient to categorize whether the patient is responsive to maintenance psychostimulants.

13. A microprocessor controlled virtual reality simulation system adapted to receive inputs generated by a user who presents a psychological disorder and/or condition for diagnosis, the system adapted to generate multidimensional information displays of three-dimensional image projections as outputs, the image projections directed to the treatment of the psychological disorder, the system comprising:

a controlling mechanism for controlling the system using a stored protocol directed to the psychological disorder, the protocol comprised of display controlling functions wherein the functions include programming commands for controlling one or more graphical elements presented on the displays;

an input mechanism adapted to accept any of a plurality of user inputs wherein the inputs are interactively entered by the user in response to the outputs presented on the displays; and an interpretation mechanism for interpreting the user inputs, applying the stored protocols to the user inputs and based thereon, controlling the output to the display wherein the output provides a presentation to the user related to treatment and/or diagnosis of the psychological disorder and/or condition.

14. The system of claim 13, wherein the protocol of display controlling functions includes programming commands for manipulating at least one three-dimensional graphical character presented as a video image projection on the displays.

15. The system of claim 13, wherein the psychological disorder for treatment is selected from the group consisting of ADHD, any ADHD subcategory, schizophrenia, depression, hyperactivity, phobias, panic attacks, anxiety, overeating, compulsive behaviors, addictions and substance abuse.

16. The system of claim 13, wherein the stored protocol is configured to provide experiential education specific for the psychological disorder.

17. The system of claim 14, wherein the psychological disorder for treatment is ADHD, and the stored protocol is configured to provide opportunities to practice focus of attention and control of impulses, supportive and performance feedback, and general information about ADHD and its treatment.

18. A method for treatment of a psychological disorder in a patient comprising the steps of:

a) providing the patient with a microprocessor controlled virtual reality simulation adapted to interact with the patient to obtain personal data related to the psychological disorder;

b) transmitting the personal data to a microprocessor controlled system, the system adapted for collecting and analyzing the data;

c) compiling a report based on the collected and analyzed data; and d) identifying criteria specific to the patient and implementing a treatment regimen for the psychological disorder.

19. The method of claim 18, wherein the psychological disorder for treatment is selected from the group consisting of ADHD, schizophrenia, depression, hyperactivity, phobias, panic attacks, anxiety, overeating, compulsive behaviors, addictions and substance abuse.

20. The method of claim 19, wherein the psychological disorder for treatment is ADHD, and the treatment regimen includes management of psychostimulant medication.

21. In a system that includes encoded electronic instructions for an interactive virtual reality simulation configured for a psychological disorder, the system being comprised of a microprocessor controlled system adapted for receiving input data from and providing a multidimensional interactive display to the patient, the system further comprising a stored protocol directed to criteria for monitoring the psychological disorder, a method for monitoring a psychological disorder in a patient comprising the steps of:

a) loading the electronic instructions into the microprocessor-based system;

b) instructing the patient on how to use the microprocessor-based unit to play the interactive virtual reality simulation; and c) monitoring the input data from the patient.

22. The method of claim 21, wherein the psychological disorder for monitoring is selected from the group consisting of ADHD, schizophrenia, depression, hyperactivity, phobias, panic attacks, anxiety, overeating, compulsive behaviors, addictions and substance abuse.

23. The method of claim 21, wherein the stored protocol is specifically configured to provide a test battery of continuous performance tasks to the patient through the interactive display, and wherein the input data from the patient responsive to the test battery is monitored to facilitate diagnoses and treatment of the psychological disorder.

24. A computer program product for controlling a computer, the program product comprising:

a computer-readable medium;

a controlling mechanism coupled to the computer-readable medium for directing the computer to generate an output signal adapted to control a video display device, the video display device equipped to display representations of three-dimensional images, wherein the output signal represents a virtual reality simulation directed to diagnosis and/or treatment of a psychological condition and/or disorder.

25. The computer program product of claim 24 wherein the computer-readable medium comprises any of a data storage device and a data receiver for receiving data from a communications link.

26. The computer program product of claim 24 further comprising a user input mechanism adapted to accept one or more inputs entered by a user presenting a possible psychological disorder and/or condition for diagnosis and/or treatment, and, in response to the one or more inputs, controlling the representations of three-dimensional images on the video display device so as to treat and/or diagnose the psychological disorder and/or condition.

27. The computer program product of claim 26 further comprising an output mechanism adapted to download one or more of the inputs entered by the user to a communications link so as to permit diagnosis and/or treatment of the psychological disorder and/or condition at a diagnostic location remote from a user location.

28. A computer program product for controlling a video display device, the program product comprising:
- a computer-readable medium;
- a controlling mechanism, coupled to the computer-readable medium, for controlling the video display device, wherein the video display device is adapted to display three-dimensional image projections, and wherein a plurality of the three-dimensional image representations represent a virtual reality simulation directed to treatment and/or diagnosis of a psychological disorder and/or condition.

* * * * *

UNITED STATES PATENT AND TRADEMARK OFFICE
CERTIFICATE OF CORRECTION

| | | |
|---|---|---|
| PATENT NO. | : 6,186,145 B1 | Page 1 of 1 |
| APPLICATION NO. | : 09/336570 | |
| DATED | : February 13, 2001 | |
| INVENTOR(S) | : Stephen J. Brown | |

It is certified that error appears in the above-identified patent and that said Letters Patent is hereby corrected as shown below:

On the title page, under "Related U.S. Application Data": change "continuation of application No. 08/247,716" to -- divisional of application No. 08/247,716 --.

Signed and Sealed this

Sixth Day of November, 2007

JON W. DUDAS
*Director of the United States Patent and Trademark Office*